US007176281B2

(12) United States Patent
Gopalakrishnakone et al.

(10) Patent No.: US 7,176,281 B2
(45) Date of Patent: Feb. 13, 2007

(54) PHOSPHOLIPASE $A_2$-INHIBITORY PEPTIDE WITH ANTI-ARTHRITIC AND NEUROPROTECTIVE ACTIVITIES

(75) Inventors: Ponnampalam Gopalakrishnakone, Singapore (SG); Maung-Maung Thwin, Singapore (SG); Wei-Yi Ong, Singapore (SG); Kazuki Sato, Higashi-ku (JP)

(73) Assignee: National University of Singapore, Crescent (SG)

( * ) Notice: Subject to any disclaimer, the term of this patent is extended or adjusted under 35 U.S.C. 154(b) by 0 days.

(21) Appl. No.: 10/836,825

(22) Filed: Apr. 30, 2004

(65) Prior Publication Data

US 2005/0069530 A1 Mar. 31, 2005

Related U.S. Application Data

(60) Provisional application No. 60/466,421, filed on Apr. 30, 2003.

(51) Int. Cl.

| | |
|---|---|
| ***A61K 38/10*** | (2006.01) |
| ***A61K 38/00*** | (2006.01) |
| ***C07K 7/00*** | (2006.01) |
| ***C12N 9/00*** | (2006.01) |
| ***A01N 37/18*** | (2006.01) |

(52) U.S. Cl. .................... 530/327; 435/69.2; 435/183; 514/2; 514/14

(58) Field of Classification Search ............... 536/23.2; 514/15, 2, 14; 435/6, 69.2, 183; 530/327
See application file for complete search history.

(56) References Cited

U.S. PATENT DOCUMENTS 6,498,242 B1 * 12/2002 Cheng et al. .............. 536/23.2

FOREIGN PATENT DOCUMENTS

WO WO 200142462 A2 * 6/2001

OTHER PUBLICATIONS

Thwin, M.M., et al. 2000 Chemistry 39: 9604-9611.*
Abstract of: G. Cirino, et al., "Recombinant Secreted Nonpancreatic Phospholipase A2 Induces a Synovitis-Like Inflammation in the Rat Air Pouch", J Rheumatol, vol. 21, No. 5, pp. 824-829 (1994).
Omar S. Jamal, et al., "Increased Expression of Human Type IIa Secretory Phospholipase $A_2$ Antigen in Arthitic Synovium", Ann. Rheum. Dis., vol. 57, pp. 550-558 (1998).
Abstract of: J.A. Green, et al., "Circulating Phospholipase A2 Activity Associated with Sepsis and Septic Shock is Indistinguishable from that Associated with Rheumatoid Arthritis", Inflammation, vol. 15, No. 5, pp. 355-367 (1991).
Abstract of M.K. Lin, et al., "Secretory Phospholipase A2 as an Index of Disease Activity in Rheumatoid Arthritis. Prospective Double Blind Study of 212 Patients", J Rheumatol, vol. 23, No. 7, pp. 1162-1166 (1966).
Timo J. Nevalainen, et al., "Roles of Secretory Phospholipase $A_2$ in Inflammatory Diseases and Trauma", Biochimica et Biophysica Acta, vol. 1488, Nos. 1-2, pp. 83-90 (2000).

(Continued)

*Primary Examiner*—Karen Cochrane Carlson
*Assistant Examiner*—Marsha Tsay
(74) *Attorney, Agent, or Firm*—Harness, Dickey & Pierce, P.L.C.

(57) ABSTRACT

Peptides that have potent $PLA_2$-inhibitory activity are disclosed. Homology searches of known PLA inhibitory molecules were used to identify and subsequently design potent peptide molecules that can induce neuroprotective as well as anti-inflammatory effect. These peptides were shown to protect against degeneration of joints in transgenic mouse model prone to arthritis. Protection from kainate-induced excitotoxic neuronal injury was also observed using these peptides. These peptides, their analogs and derivatives have potential as neuroprotective and/or anti-inflammatory agents in a clinical setting.

35 Claims, 14 Drawing Sheets

OTHER PUBLICATIONS

Anna M. Planas, et al., "Induction of Cyclooxygenase-2 mRNA and Protein Following Transient Focal Ischemia in the Rat Brain", Neuroscience Letters, vol. 200, pp. 187-190 (1995).

Akhlaq A. Farooqui, et al., "Involvement of Phospholipase $A_2$ in Neurodegeneration", Neurochem. Int., vol. 30, No. 6., pp. 517-522 (1997).

T.L. Sandhya, et al., "A Light and Electron Microscopic Study of Cytoplasmic Phospholipase $A_2$ and Cyclooxygenase-2 in the Hippocampus after Kainate Lesions", Brain Research, vol. 788, pp. 223-231 (1998).

Xin-Rong Lu, et al., "Differential Effects of Calcium-Dependent and Calcium-Independent Phospholipase $A_2$ Inhibitors on Kainate-Induced Neuronal Injury in Rat Hippocampal Slices", Free Radical Biology & Medicine, vol. 30, No. 11, pp. 1263-1273 (2001).

Akhlaq A. Farooqui, et al., "Inhibitors of Intracellular Phospholipase $A_2$ Activity: Their Neurochemical Effects and Therapeutical Importance for Neurological Disorders", Brain Research Bulletin, vol. 49, No. 3, pp. 139-153 (1999).

Tatsurou Yagami et al., "Human Group IIA Secretory Phospholipase $A_2$ Induces Neuronal Cell Death via Apoptosis", Molecular Pharmacology, vol. 61, No. 1, pp. 114-126 (2002).

Abstract of: J. Balsinde, et al., "Regulation and Inhibition of Phospholipase A2", Annu. Rev. Pharmacol. Toxicol., vol. 39 pp. 175-189 (1999).

M.-M. Thwin, et al., "Recombinant Antitoxic and Antiinflammatory Factor from the Nonvenomous Snake *Python reticulatus*: Phospholipase $A_2$ Inhibition and Venom Neutralizing Potential", Biochemistry, vol. 39, pp 9604-9611 (2000).

Muang-Maung Thwin, et al., "Functional Site of Endogenous Phospholipase $A_2$ Inhibitor from Python Serum, Phospholipase $A_2$ Binding and Anti-Inflammatory Activity", Eur. J. Biochem., vol. 269, pp. 719-727 (2002).

David W. Snyder, et al., "Pharmacology of LY315920/S-5920,[1] [[3-(Aminooxacetyl)-2-ethyl-1-(phenylmethyl)-1*H*-indol-4-yl]oxy]acetate, a Potent and Selective Secretory Phospholipase $A_2$ inhibitor: A New Class of Anti-Inflammatory Drugs, SPI", The Journal of Pharmacology and Experimental Therapeutics, vol. 288, No. 3, pp. 1117-1124 (1999).

Abstract of: E. Abraham, et al., "Efficacy and Safety of LY315920Na/S-5920, a Selective Inhibitor of 14-kDa Group IIA Secretory Phospholipase A2, in Patients with Suspected Sepsis and Organ Failure", Crit. Care Med., vol. 31, No. 3, pp. 718-728 (2003).

Abstract of P. Kortekangas, et al., "Group II Phospholipase A2 in Synovial Fluid and Serum in Acute Arthritis", Scand. J Rheumatol, vol. 23, No. 2, pp. 68-72 (1994).

Abstract of P. Vadas, et al., "Induction of Group II Phospholipase A2 Expression and Pathogenesis of the Sepsis Syndrome", Circ. Shock., vol. 39, No. 2, pp. 160-167 (1993).

Abstract of: T.J. Nevalainen, et al., "Pancreatic and Synovial Type Phospholipases A2 in Serum Samples from Patients with Severe Acute Pancreatitis", Gut., vol. 34, No. 8, pp. 1133-1136 (1993).

L. Stoppini, et al., "A Simple Method for Organotypic Cultures of Nervous Tissues", Journal of Neuroscience Methods, vol. 37, pp. 173-182 (1991).

* cited by examiner

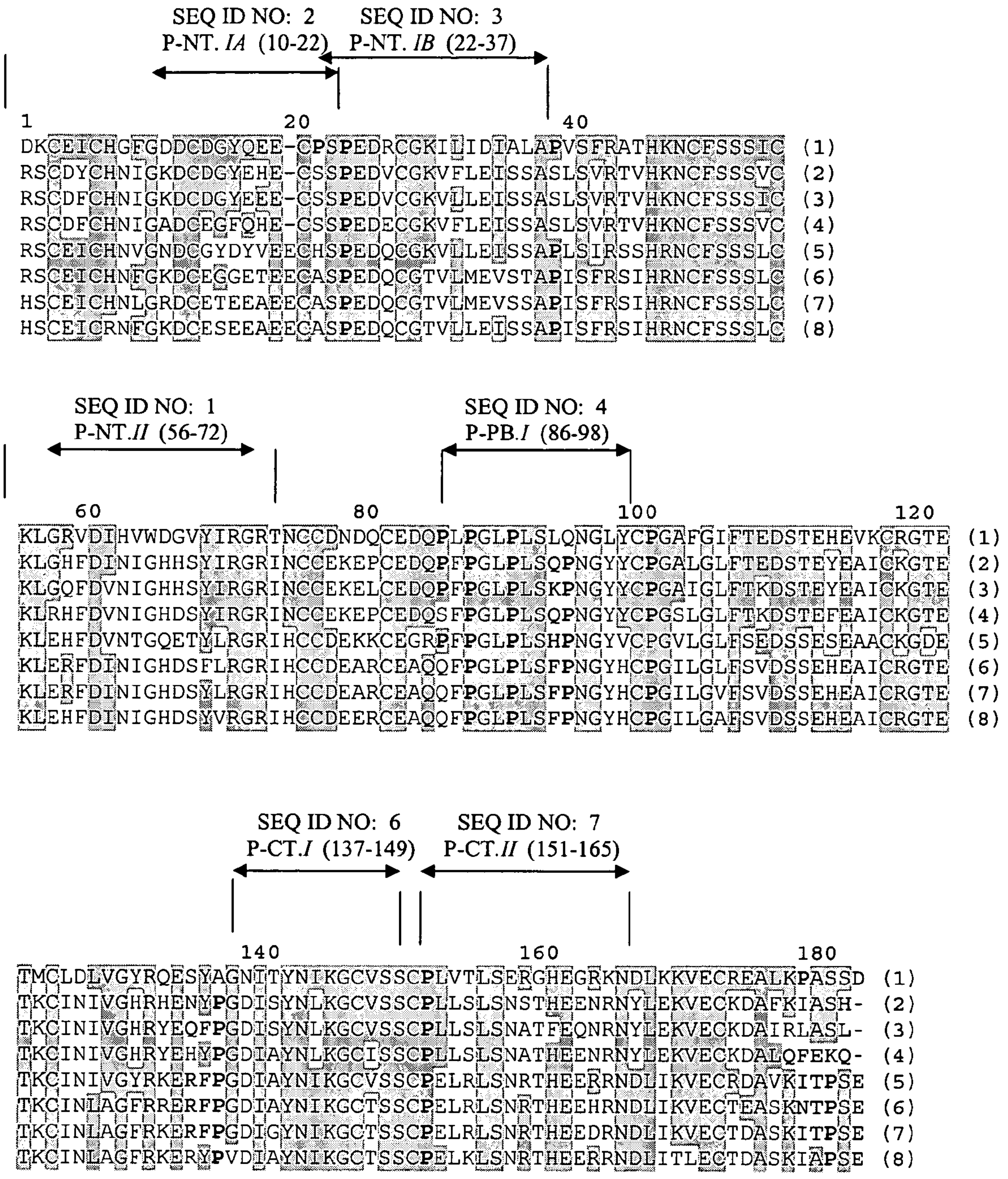

FIGURE 1

```
                SEQ ID NO: 2      SEQ ID NO: 3
                P-NT.IA (10-22)   P-NT.IB (22-37)

1                        20                            40
DKCEICHGFGDDCDGYQEE-CPSPEDRCGKILIDIALAPVSFRATHKNCFSSSIC  (1)
RSCDYCHNIGKDCDGYEHE-CSSPEDVCGKVFLEISSASLSVRTVHKNCFSSSVC  (2)
RSCDFCHNIGKDCDGYEEE-CSSPEDVCGKVLLEISSASLSVRTVHKNCFSSSIC  (3)
RSCDFCHNIGADCEGFQHE-CSSPEDECGKVFLEISSASLSVRTVHKNCFSSSVC  (4)
RSCEICHNVGNDCGYDYVEECHSPEDQCGKVLLEISSAPLSIRSSHRNCFSSSLC  (5)
RSCEICHNFGKDCEGGETEECASPEDQCGTVLMEVSTAPISFRSIHRNCFSSSLC  (6)
HSCEICHNLGRDCETEEAEECASPEDQCGTVLMEVSSAPISFRSIHRNCFSSSLC  (7)
HSCEICRNFGKDCESEEAEECASPEDQCGTVLLEISSAPISFRSIHRNCFSSSLC  (8)

   SEQ ID NO: 1                         SEQ ID NO: 4
   P-NT.II (56-72)                      P-PB.I (86-98)

          60            80            100           120
KLGRVDIHVWDGVYIRGRTNCCDNDQCEDQPLPGLPLSLQNGLYCPGAFGIFTEDSTEHEVKCRGTE (1)
KLGHFDINIGHHSYIRGRINCCEKEPCEDQPFPGLPLSQPNGYYCPGALGLFTEDSTEYEAICKGTE (2)
KLGQFDVNIGHHSYIRGRINCCEKELCEDQPFPGLPLSKPNGYYCPGAIGLFTKDSTEYEAICKGTE (3)
KLRHFDVNIGHDSYIRGRINCCEKEPCEDQSFPGLPLSQPNGYYCPGSLGLFTKDSTEFEAICKGTE (4)
KLEHFDVNTGQETYLRGRIHCCDEKKCEGRPFPGLPLSHPNGYVCPGVLGLFSEDSSESEAACKGDE (5)
KLERFDINIGHDSFLRGRIHCCDEARCEAQQFPGLPLSFPNGYHCPGILGLFSVDSSEHEAICRGTE (6)
KLERFDINIGHDSYLRGRIHCCDEARCEAQQFPGLPLSFPNGYHCPGILGVFSVDSSEHEAICRGTE (7)
KLEHFDINIGHDSYVRGRIHCCDEERCEAQQFPGLPLSFPNGYHCPGILGAFSVDSSEHEAICRGTE (8)

           SEQ ID NO: 6      SEQ ID NO: 7
           P-CT.I (137-149)  P-CT.II (151-165)

                140           160           180
TMCLDLVGYRQESYAGNITYNIKGCVSSCPLVTLSERGHEGRKNDLKKVECREALKPASSD (1)
TKCINIVGHRHENYPGDISYNLKGCVSSCPLLSLSNSTHEENRNYLEKVECKDAFKIASH- (2)
TKCINIVGHRYEQFPGDISYNLKGCVSSCPLLSLSNATFEQNRNYLEKVECKDAIRLASL- (3)
TKCINIVGHRYEHYPGDIAYNLKGCISSCPLLSLSNATHEENRNYLEKVECKDALQFEKQ- (4)
TKCINIVGYRKERFPGDIAYNIKGCVSSCPELRLSNRTHEERRNDLIKVECRDAVKITPSE (5)
TKCINLAGFRRERFPGDIAYNIKGCTSSCPELRLSNRTHEEHRNDLIKVECTEASKNTPSE (6)
TKCINLAGFRKERFPGDIGYNIKGCTSSCPELRLSNRTHEEDRNDLIKVECTDASKITPSE (7)
TKCINLAGFRKERYPVDIAYNIKGCTSSCPELKLSNRTHEERRNDLITLECTDASKIAPSE (8)
```

FIGURE 3.
(A)
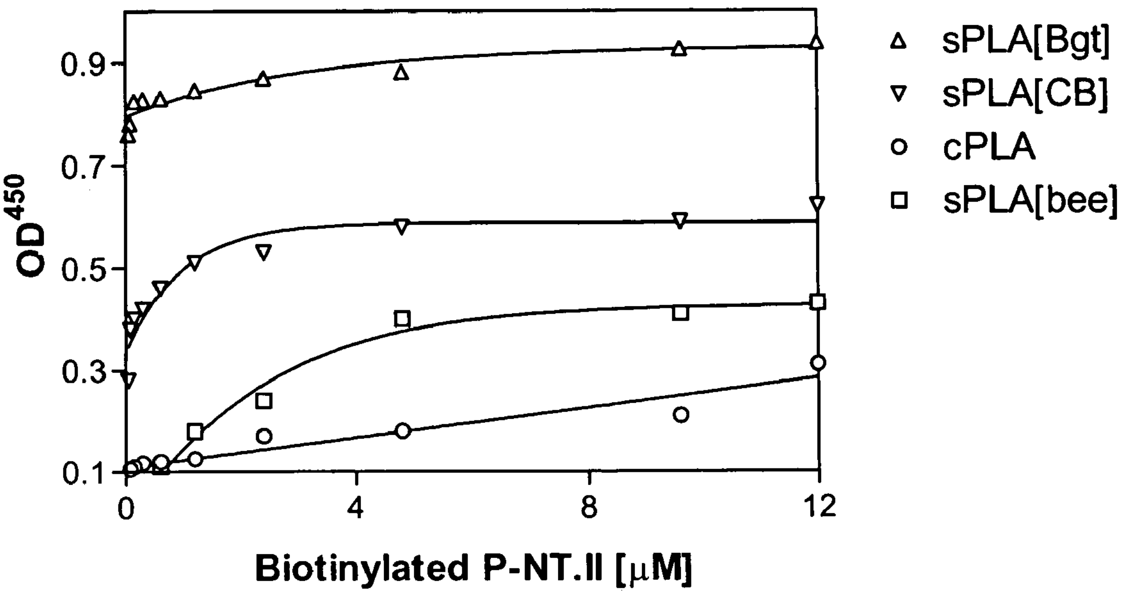
(B)
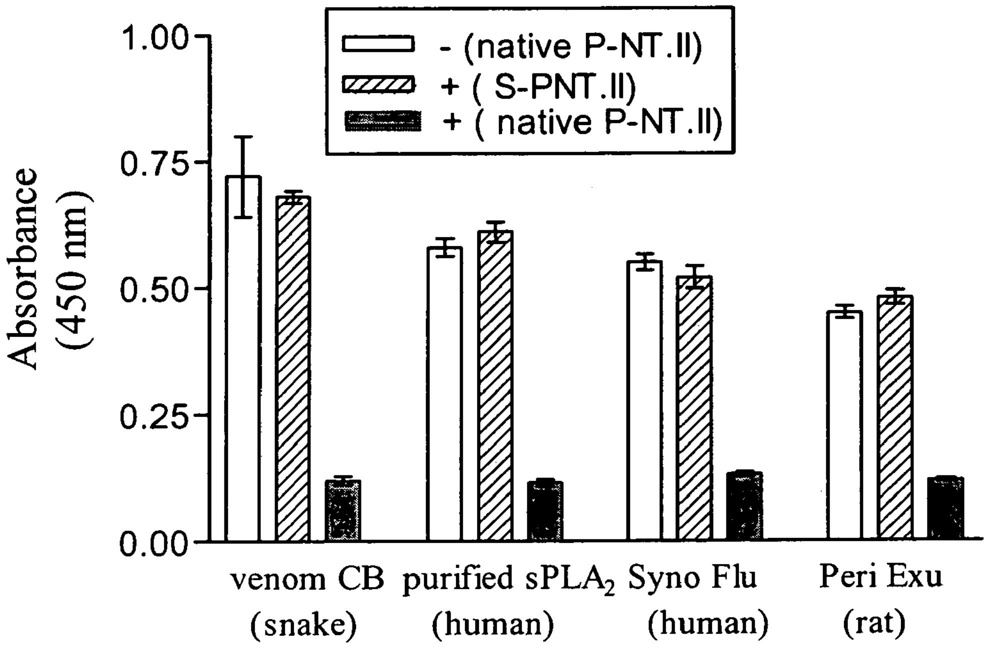

FIGURE 13
(A)
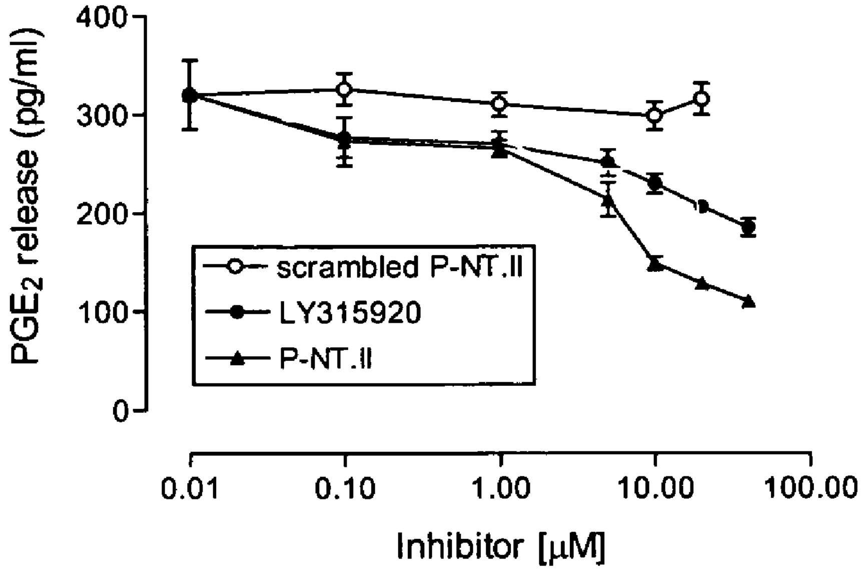
(B)
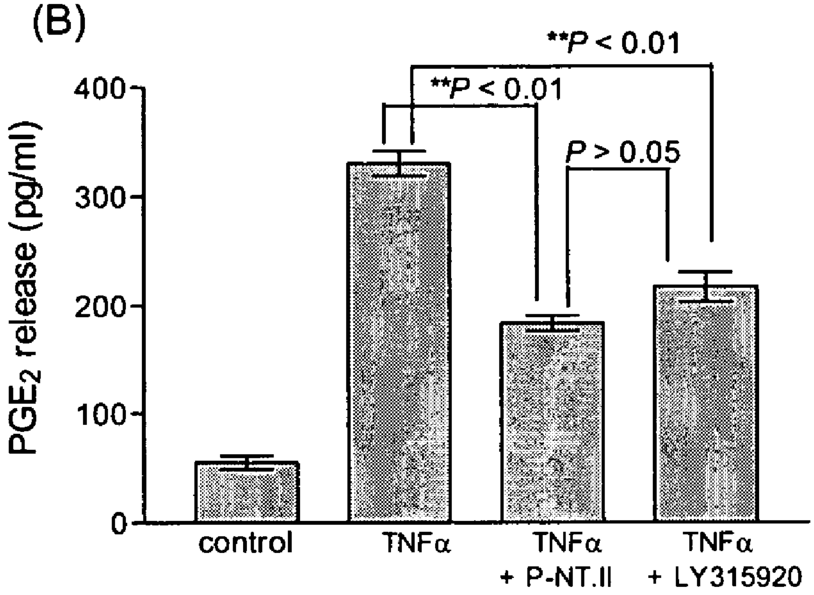

PIP[59-67] dimer.................................. $IC_{50}$ = 1.19 micromolar
LY315920.......................................... $IC_{50}$ = 2.29 micromolar

PHOSPHOLIPASE $A_2$-INHIBITORY PEPTIDE WITH ANTI-ARTHRITIC AND NEUROPROTECTIVE ACTIVITIES

This application claims the benefit of U.S. Provisional Application No. 60/466,421 filed on $30^{th}$ Apr. 2003 the contents of which in its entirety are incorporated by reference herein.

TECHNICAL FIELD

The invention relates to novel peptide molecules and more specifically to a phospholipase A-inhibitory peptide, its synthetic homologs and derivatives thereof.

BACKGROUND

Group IIA Secretory phospholipase ($sPLA_2$-IIA) is known to be proinflammatory in vivo (Cirino, G., et al. (1994) *J. Rheumatol.* 21, 824–829), and concentration of this enzyme in serum and in tissues correlates with disease severity in several immune-mediated inflammatory pathologies in humans and rats. It is associated with the onset of rheumatoid arthritis (Jamal, O. S., et al. (1998) *Ann. Rheum. Dis.* 57, 550–558) and septic shock (Green, J.-A., et al. (1991) *Inflammation* 15, 355–367). Levels of $sPLA_2$ in synovial fluid also correlate with severity of disease in rheumatoid arthritis patients (Lin, M. K. S., et al. (1996) *J. Rheumatol.* 23, 1162), and the concentration of $PLA_2$-IIA increases in blood plasma in generalized inflammatory response resulting from infections, chronic inflammatory diseases, acute pancreatitis, trauma and surgical operations (Nevalainen, T. J., et al. (2000) *Biochim. et Biophys. Acta.* 1488 (1–2), 83–90). Hence, inhibition of $PLA_2$ may logically, block the formation of a wide variety of secondary inflammatory mediators. The central role of $PLA_2$ in inflammation thus makes the enzyme a potential target for drug development.

A number of studies have indicated that $PLA_2$ and COX enzymes play an important role in the neurodegenerative processes associated with excitotoxic, ischemic, and traumatic brain injuries and neurodegenerative diseases (Palanas, A. M., et. al. (1995) *Neurosci. Lett.* 200, 187–190; Farooqui, A. A. et al. (1997) *Neurochem. Int.* 30, 517–522). In excitotoxic neuronal injury, levels of cytosolic phospholipase $A_2$s ($cPLA_2$s) is known to increase significantly (Sandhya, T. L. et al. (1998). *Brain Res.* 788, 223–231), and $cPLA_2$ inhibitors have been shown to protect excitotoxic neuronal injury in hippocampal slice cultures (Lu, X.-R. et al. (2001). *Free Rad. Biol. Med.* 30, 1263–1273; Farooqui, A. A. et al. (1999). *Brain Res. Bull.* 49, 139–53). Besides $cPLA_2$, $sPLA_2$ has also been suggested to induce neuronal cell death via apoptosis which might be associated with arachidonic acid metabolites, especially $PGD_2$, thus highlighting the therapeutic potential of $sPLA_2$ inhibitors for stroke (Yagami, T. et al (2002) *Mol. Pharmacol.* 61, 114–126).

Most of the currently available $PLA_2$ inhibitors such as scalaradial, BEL, AACOCF3 are molecules that are not suited for sustained biological intervention within the body. Moreover, the possibility of their generating antibodies that would neutralize the effect of the molecule are also significant. The need for an effective molecule that can inhibit the biological effect of secretory and/or cytosolic $PLA_2$ is thus largely unmet.

SUMMARY

It is thus an object of an embodiment of the instant invention to provide potent molecules capable of inhibiting both secretory and cytosolic phospholipase $A_2$ enzyme activity.

Another aspect of the invention provides peptide molecules that are neuroprotective by inhibiting cytosolic phospholipase $A_2$ activity resulting in reduced neuronal damage.

In accordance with yet another aspect of the invention, peptide molecules that can reduce inflammatory damage by inhibiting secretory phospholipase $A_2$ activity are provided.

In accordance with one aspect of the invention is provided, an isolated peptide molecule capable of inhibiting $cPLA_2$ and/or $sPLA_2$ activity in a mammal and comprising the amino acid sequence as set forth in SEQ ID NO. 1.

Another aspect of the invention provides an isolated peptide molecule comprising the amino acid sequence as set forth in SEQ ID NO. 8, capable of inhibiting $cPLA_2$ and/or $sPLA_2$ activity in a mammal.

An isolated peptide molecule comprising the amino acid sequence as set forth in SEQ ID NO. 9, and which is capable of inhibiting $cPLA_2$ and/or $sPLA_2$ activity in a mammal, is provided.

According to yet another aspect of the invention, a $PLA_2$-inhibitory peptide derivative of the amino acid sequence as set forth in SEQ ID NO. 8 is provided, wherein aspartic acid is substituted with glutamic acid.

Another aspect of the invention provides $PLA_2$-inhibitory peptide that is either a derivative or fragment of the peptide sequence as set forth in SEQ ID NO. 1.

Also provided according to an aspect of the invention are fragments and derivative peptides comprising an amino acid sequence as set forth in any one of SEQ ID NOs. 2–7, capable of inhibiting $PLA_2$ activity in a mammal.

Yet another aspect of the invention provides polynucleotide sequences as set forth in SEQ ID NO. 10 that encode $PLA_2$-inhibitory peptide sequences.

Another aspect provides for a composition capable of inhibiting $PLA_2$ activity, comprising at least one $PLA_2$-inhibitory peptide comprising an amino acid sequence as set forth in any one of SEQ ID NOs. 1–9.

Yet another aspect of the invention provides peptide molecules that can bind to any one of the amino acid sequences as set forth in SEQ ID NOs 1–9.

One aspect of the invention provides a method of treatment or prophylaxis of an inflammatory disorder, neuronal injury or cancer by inhibiting the activity of $sPLA_2$, comprising administering to the subject, a therapeutically or prophylactically effective dose of a composition comprising at least one $PLA_2$-inhibitory peptide disclosed herein.

Yet another aspect of the invention provides a method of treating or preventing neuronal injury resulting from neurodegenerative disease, trauma, excitotoxic effect or ischemia by inhibiting the enzymatic activity of secretory and cytosolic $PLA_2$ in the afflicted individual.

A method of making $sPLA_2$-inhibitory peptide by the recombinant route is provided according to a final aspect of the invention, comprising cloning and expressing the polynucleotide sequence as set forth in SEQ ID NO 10 into a suitable expression vector and isolating the expressed polypeptide.

These and other advantages of the present invention will become readily apparent upon review of the following detailed description of the invention and the claims.

DETAILED DESCRIPTION OF THE DRAWINGS

FIG. 1 shows the alignment of the amino acid sequences of PIP with sequences in the protein databases.

FIGS. 3A and 3B show ELISA results using biotinylated P-NT.II and different $PLA_2$s showing binding specificities. In FIG. 3A, the ELISA results were obtained using biotinylated P-NT.II directed against human recombinant $cPLA_2$, venom $sPLA_2$s, β-bungarotoxin, crotoxin B and bee venom $PLA_2$. In FIG. 3B, the ELISA results were obtained using biotinylated P-NT.II directed against $sPLA_2$s representing mammalian type IIA.

Figure 4:
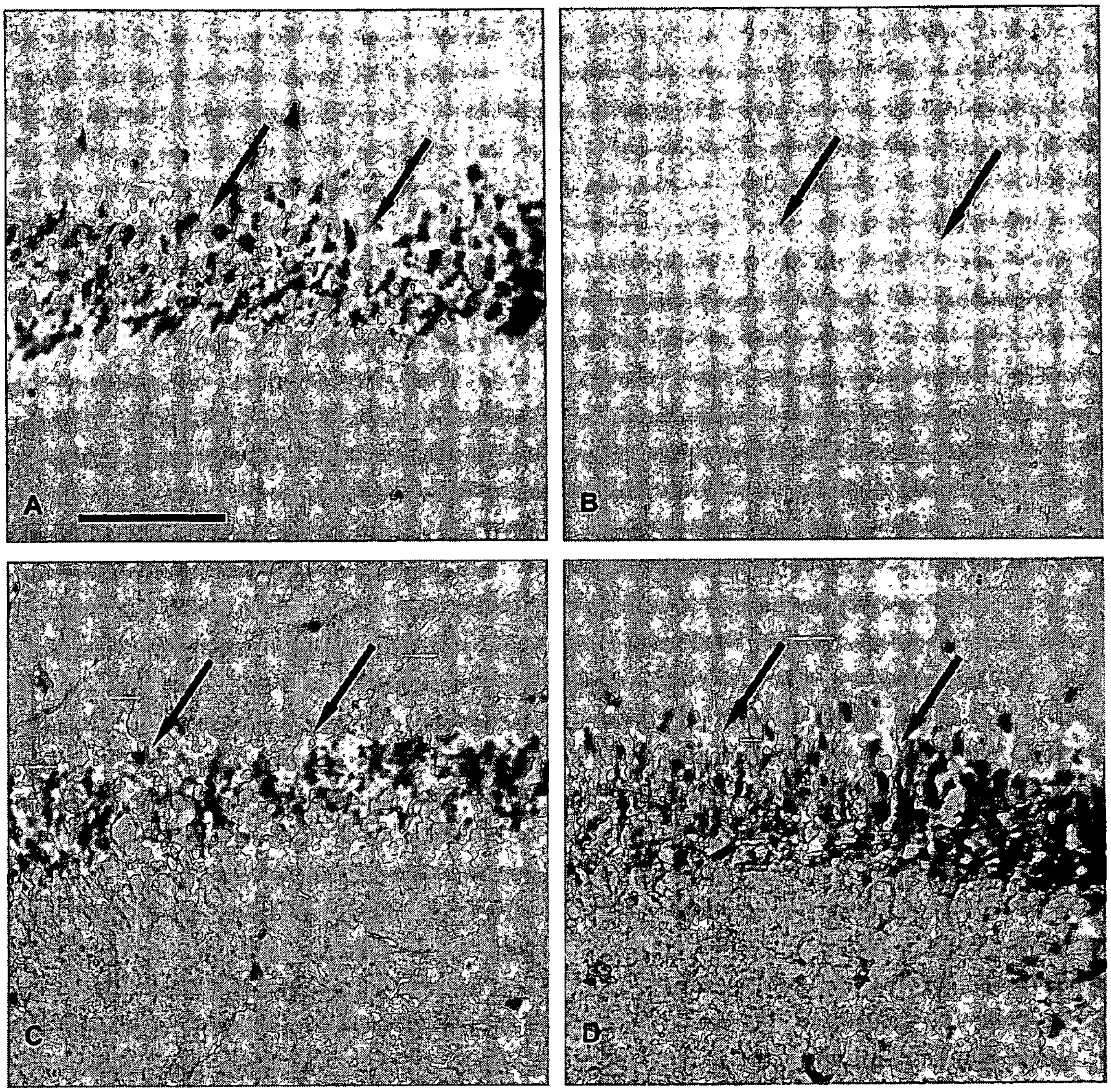

FIGS. 4A to 4D show neuronal marker-stained hippocampal tissue sections demonstrating dense staining for controls as compared to sparse staining in kainate-treated ones. FIG. 4A shows a tissue section of a hippocampal slice treated only with DMSO, as a vehicle control. FIG. 4B shows a tissue section of a hippocampal slice treated with kainite. FIG. 4C shows a tissue section of a hippocampal slice pre-treated with 12-epi-scalaradial followed by treatment with kainite. FIG. 4D shows a tissue section of a hippocampal slice pre-treated with PNT-II peptide followed by treatment with kainite.

Figure 5:
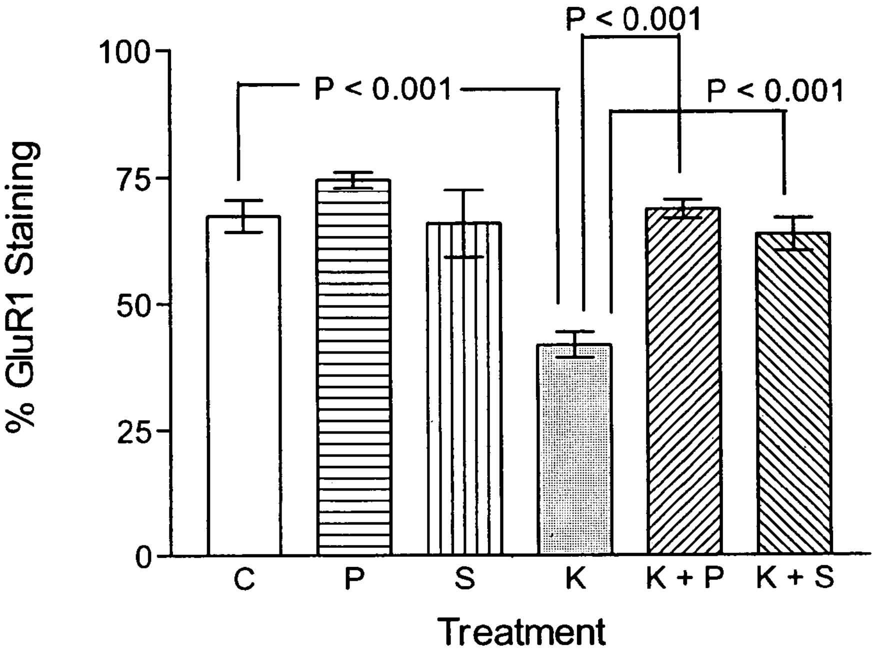

FIG. 5 shows a histogram depicting the effect of inhibitors on kainite-induced hippocampal lesions.

FIGS. 6A to 6F show histologies of ankle-joints in untreated and P-NT.II-treated transgenic mice. FIGS. 6A and 6B show the histologies of ankle joints of untreated Tg197 mice. FIGS. 6C and 6D show the histologies of ankle joints of P-NT.II-treated mice. FIGS. 6E and 6F show the histologies of ankle joints of scrambled P-NT.II-treated mice.

FIGS. 7A to 7C show histological scores of transgenic untreated mice and mice treated with P-NT.II for 5 weeks. FIG. 7A represents mean (±SE) histological scores taken from 8 mice (4 males and 4 females) (n=16 ankle joints). FIG. 7B represents mean (±SE) histological scores taken from 4 male mice (n=8 ankle joints). FIG. 7C represents mean (±SE histological scores taken from 4 female mice (n=8 ankle joints).

Figure 8:
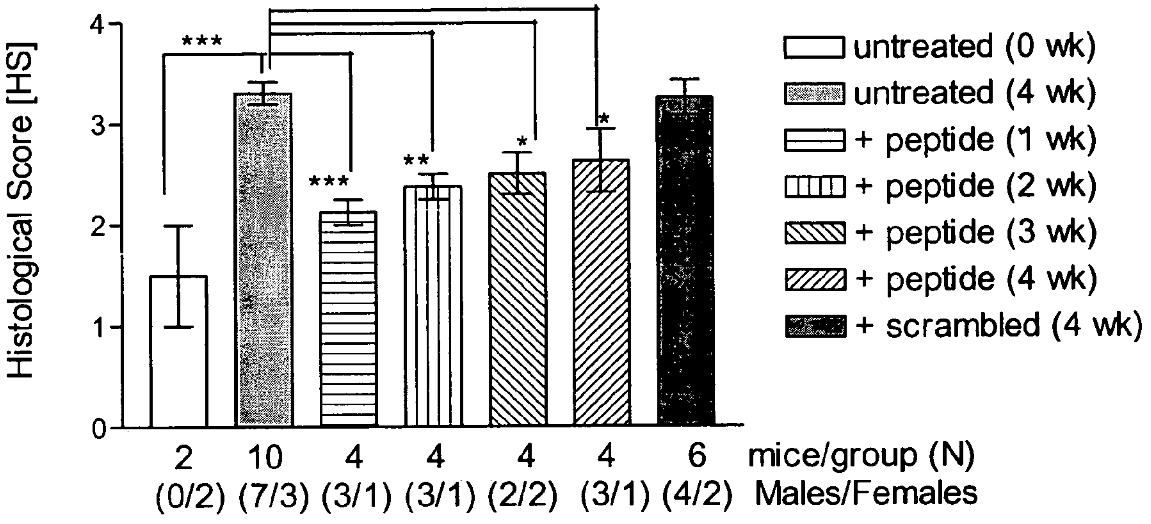
Figure 9:
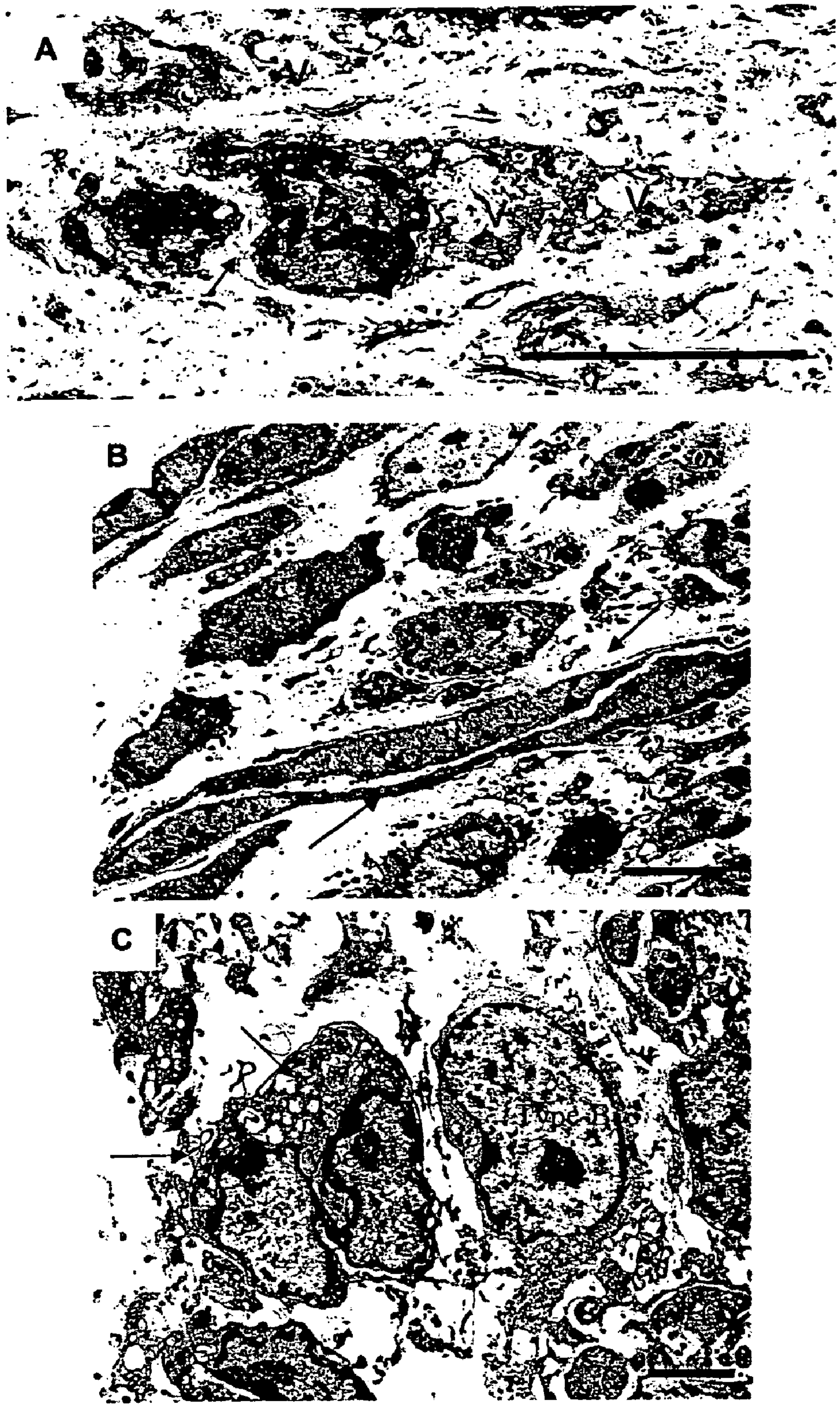

FIG. 8 shows histological scores of transgenic mice with time-course at pre- and 1–4 weeks of treatment with P-NT.II peptide FIGS 9A to 9C show comparative cytological features of synoviocytes of treated animals and those that were untreated or administered the scrambled peptide. FIGS. 9A and 9B show the cytological features of synoviocytes of untreated Tg197 mice. FIG. 9C shows the cytological features of synoviocytes of peptide-treated T197 mice.

Figure 10:
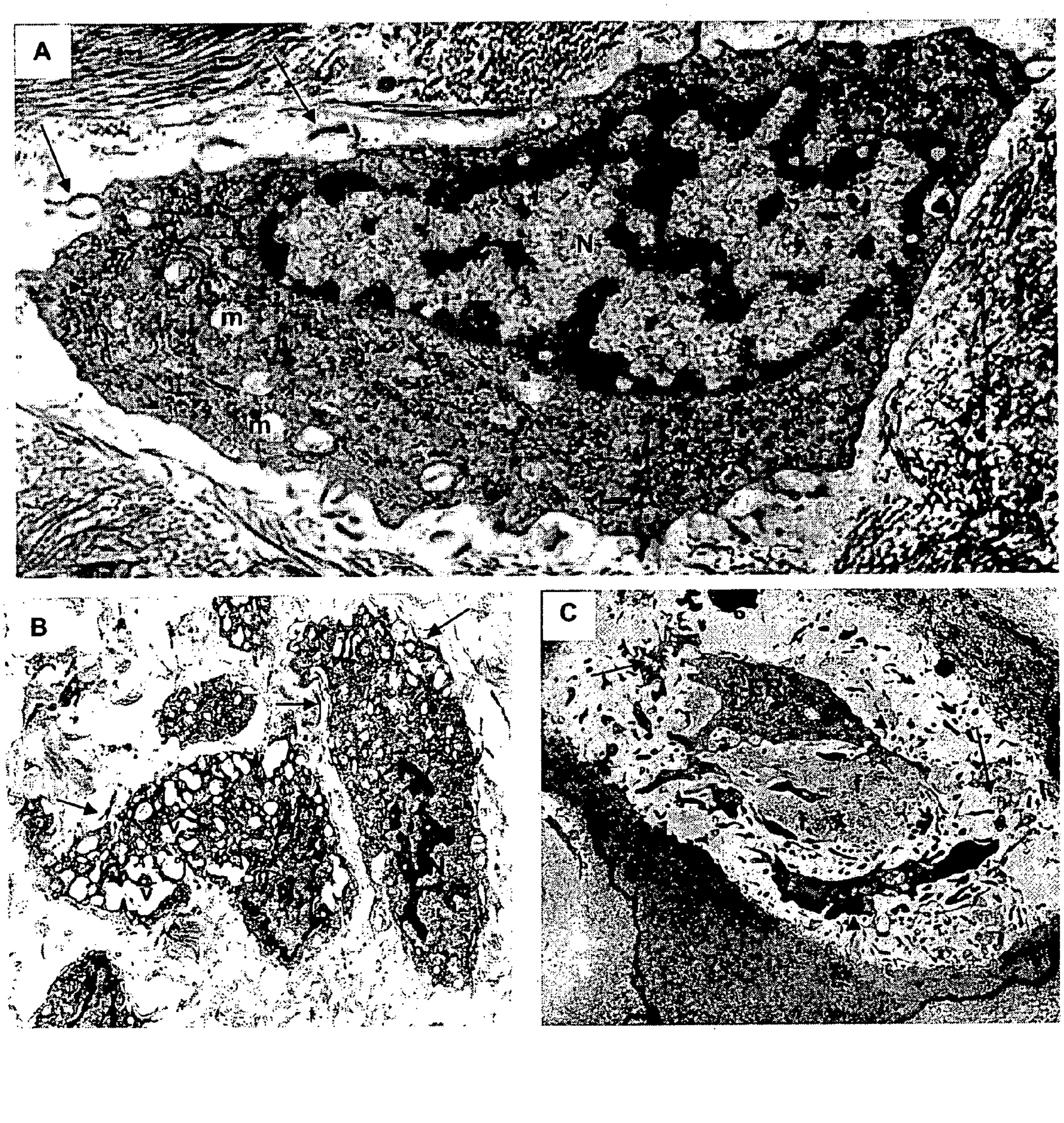

FIGS. 10A to 10C show chondrocytes of treated and untreated T197 mice. FIG. 10A shows the articular chondrocytes of peptide-treated Tg197 mice.

FIG. 10B shows the articular chondrocytes of scrambled peptide-treated Tg197 mice.

FIG. 10C shows degenerated chondrocytes of untreated Tg197 mice.

Figure 11:
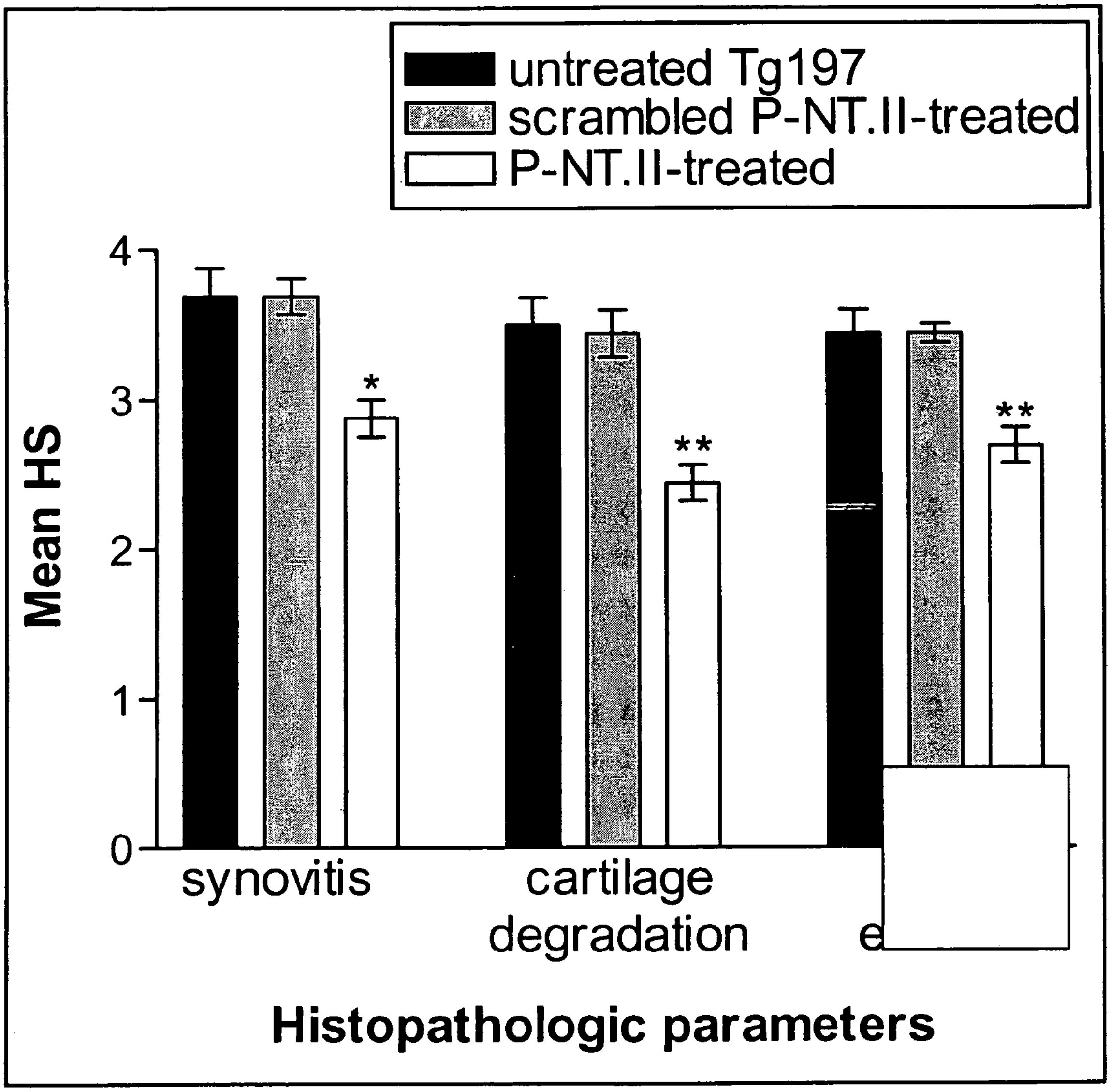

FIG. 11 shows the analysis of various histopathologic parameters of untreated and P-NT.II-treated animals.

Figure 12:
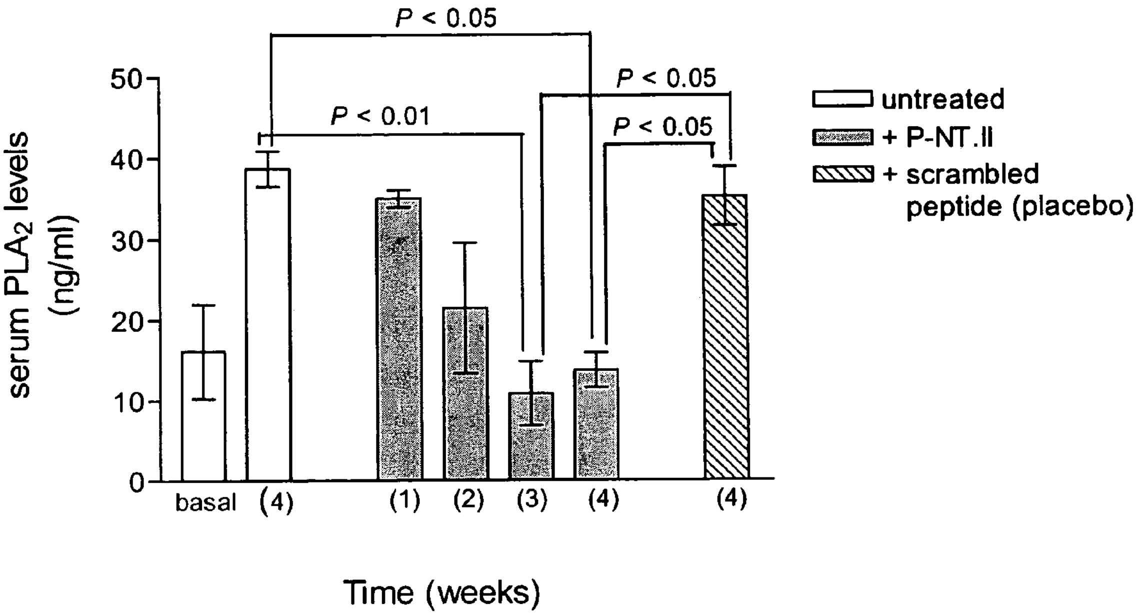

FIG. 12 shows time-course of serum $sPLA_2$ levels using *E. coli* membrane assay.

FIGS. 13A and 13B show modulation of LPS- and TNF-stimulated PGE release by P-NT.II. In FIG. 13A, the results were obtained by incubating a J774 mouse cell line with LPS and varying concentrations (0–40 μM) of P-NT.II, LY315920 or scrambled P-NT.II, and collecting the resulting supernatants for determination of $PGE_2$ release. In FIG. 13B, the results were obtained by stimulating the J774 mouse cell line with mouse recombinant TNF and 10 μM P-NT.II, LY315920 or scrambled P-NT.II, and collecting the resulting supernatants for determination of $PGE_2$ release.

Figure 14:
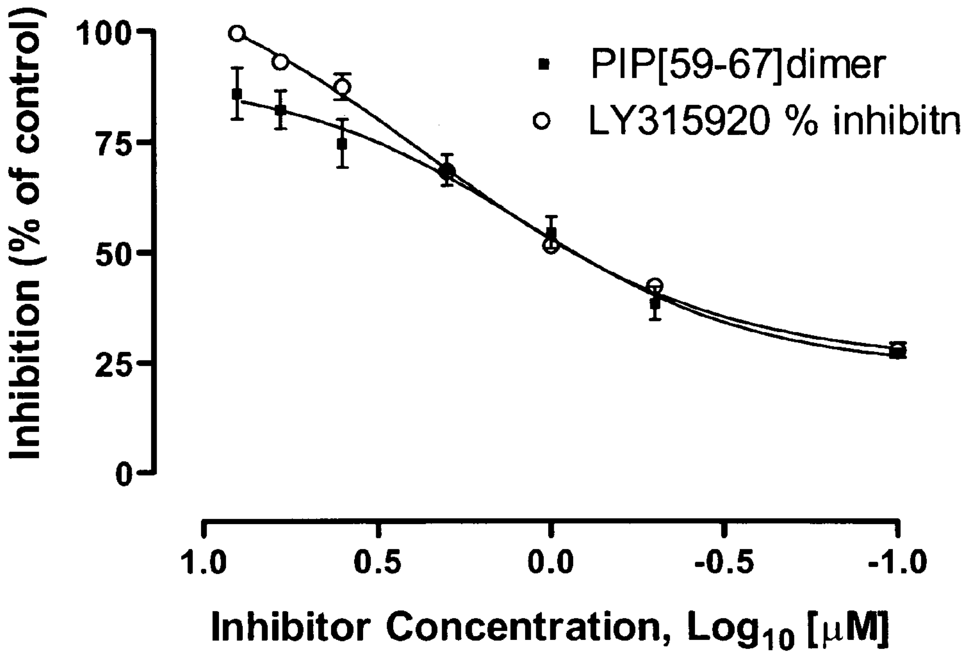

FIG. 14 shows inhibition profiles of PIP (59–67) dimer and LY315920 analog against enzymatic activity of purified human synovial $sPLA_2$

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "expression vector" is meant any autonomous genetic element capable of directing the synthesis of a protein encoded by the vector. Such expression vectors are known to practitioners in the art.

As used herein, the term "function" refers to a biological, enzymatic, or therapeutic function.

"Homology" refers to the percentage number of amino acids that are identical or constitute conservative substitutions. Homology may be determined using sequence comparison programs.

By "effective amount" is meant the administration to an animal of an amount of a peptide, fragment, variant or derivative molecule of the invention, either in a single dose or as part of a series, that is effective for eliciting an inhibitory response against $PLA_2$ molecule. The effective amount will vary depending upon the taxonomic group of animal to be treated, the immune status of the subject, age and body weight of the recipient and the formulation of the composition. It is expected that the amount will fall in a relatively broad range that can be determined through routine trials. By "isolated" is meant material that is substantially or essentially free from components that normally accompany it in its native state. e.g., a polypeptide fragment which has been removed from the sequences which are normally adjacent to the fragment.

By "pharmaceutically-acceptable carrier" is meant a solid or liquid filler, diluent or encapsulating substance that can be safely used in delivering the $PLA_2$ inhibitory peptide of the invention by oral, topical or systemic administration to a recipient.

By "peptide" is meant a molecule composed of amino acids that may be derived from natural sources, or artificially synthesized such as by using a peptide synthesizer.

The term "derivative" refers to peptides in which one or more amino acids have been replaced by different amino acids and which retains the function or activity of the original peptide. It is well understood in the art that some amino acids may be changed to others with broadly similar properties without changing the nature of the function or activity of the polypeptide (conservative substitutions) as described hereinafter.

The invention also contemplates polypeptide variants of the antitoxic polypeptide of the invention wherein said variants neutralise or inhibit a venom or toxin. Suitable methods of testing such activity are provided in Section 2.1 of PCT/SG00/00201 (now WO 01/42462). In general, variants will be at least 75% homologous, more suitably at least 80%, preferably at least 85%, and more preferably at least 90% homologous to a polypeptide as for example shown in SEQ ID NO: 2 or 6.

Suitable polypeptide variants may be identified by replacing at least one amino acid of a parent polypeptide (e.g., a polypeptide according to SEQ ID NO: 2 or 6) with a different amino acid to produce a modified polypeptide, combining the modified polypeptide with a phospholipase A2; and detecting the presence of a conjugate comprising the modified polypeptide and the phospholipase A2. If a conjugate is formed comprising the modified polypeptide and the phospholipase A2, this is indicative of the modified polypeptide being a variant of the parent polypeptide.

Polypeptide variants may also be identified by administering a modified polypeptide as defined above to an animal and subsequently challenging the animal with a dosage of a venom or toxin, which dosage in the absence of the modified polypeptide invokes lethality or disease in the animal. If modified polypeptide protects against lethality or disease in the animal, this is indicative of the modified polypeptide being a polypeptide variant according to the invention.

Alternatively, suitable variants may be obtained by combining a modified polypeptide as defined above with an antigen-binding molecule that binds to a parent polypeptide or biological fragment on which the modified polypeptide is based, and preferably to a domain of the parent polypeptide or fragment that binds a phospholipase A2 molecule. If a conjugate is formed comprising the modified polypeptide and the phospholipase A2, this may be indicative of the modified polypeptide being a variant of the parent polypeptide or fragment.

Polypeptide variants according to the invention can be identified either rationally, or via established methods of mutagenesis (see, for example, Watson, J. D. et al., "MOLECULAR BIOLOGY OF THE GENE", Fourth Edition, Benjamin/Cummings, Menlo Park, Calif., 1987). Significantly, a random mutagenesis approach requires no a priori information about the gene sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow, R. 1986, *J. Prot. Eng.* 1: 7–16; Knowles, J. R., 1987, *Science* 236: 1252–1258; Shaw, W. V., 1987, *Biochem. J.* 246:1–17; Gerit, J. A. 1987, *Chem. Rev.* 87:1079–1105). Alternatively, where a particular sequence alteration is desired, methods of site directed mutagenesis can be employed. Thus, such methods may be used to selectively alter only those amino acids of the protein that are believed to be important (Craik, C. S., 1985, *Science* 228: 291–297; Cronin, et al., 1988, *Biochem.* 27: 4572–4579; Wilks, et al., 1988, *Science* 242: 1541–1544).

Variant peptides or polypeptides, resulting from rational or established methods of mutagenesis or from combinatorial chemistries as hereinafter described, may comprise conservative amino acid substitutions. Exemplary conservative substitutions in an immuno-interactive polypeptide or polypeptide fragment according to the invention may be made according to the following TABLE A:

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE A. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp); or (d) a residue having a bulky side chain (e.g., Phe or Trp) is substituted for, or by, one having a smaller side chain (e.g., Ala, Ser) or no side chain (e.g., Gly).

By "fragment" is meant a portion or truncated form of a peptide molecule that retains the function or activity of the original peptide of which it forms a part.

The term "recombinant polynucleotide" or "synthetic polynucleotide" refers to a polynudeotide formed in vitro by the manipulation of nucleic acid into a form not normally found in nature. For example, the recombinant or synthetic polynucleotide may be in the form of an expression vector. Generally, such expression vectors include transcriptional and translational regulatory nucleic acid operably linked to the nucleotide sequence.

By "recombinant peptide" is meant a peptide made using recombinant techniques, i.e., through the expression of a recombinant or synthetic polynucleotide.

DETAILED DESCRIPTION

Since the discovery that mammalian $PLA_2$ is a key enzyme in the release of arachidonic acid, the substrate for the synthesis of several lipid inflammatory mediators, much interest has been focused on this enzyme in the context of inflammation. The mechanisms involved in the proinflammatory action of secretory $PLA_2$s are being actively investigated, and part of the knowledge on secretory $PLA_2$ effects has been gained by using snake venom $PLA_2$s as tools, due to their high structural homology with human secretory $PLA_2$s.

$PLA_2$ are enzymes that catalyse the hydrolysis of the sn-2 acyl bond of glycerophospholipids to produce free fatty acids and lysophospholipids and are implicated in a range of diseases associated with inflammatory conditions such as arthritis, peritonitis, etc. Furthermore, $PLA_2$ inhibitors (PLIs) have recently become the subject of much interest due to the potential benefits they could offer in the treatment of inflammation and cell injury. A number of PLIs have been purified and characterized from a variety of sources, including plant, fungi, and bacteria. PLIs that interact with $PLA_2$s and inhibit their enzymatic activity have been identified in the sera of venomous snakes belonging to Elapidae and Crotalidae families. The discovery of specific s $PLA_2$ inhibitors has also been reported in the blood serum of non-venomous snakes. Three types of PLIs are known in the sera of snakes, which are believed to have a natural defensive role against endogenous snake venom $sPLA_2$s.

A number of $PLA_2$ inhibitors have been proposed as potential drugs for the treatment of inflammatory conditions. These include cell-permeable inhibitors that might interfere with the vital PL metabolism, carried out by the intracellular $PLA_2$s, and impair the cell viability. It is thus desirable to control the $sPLA_2$ activity, which plays a major role in pathological conditions but not in the normal PL metabolism. A specific inhibitor of type $sPLA_2$ has recently been developed for this purpose, but since more than one type of $sPLA_2$ play a role in inflammatory processes, it is desirable to inhibit the different sPLA2s. Accordingly, there is a clear advantage to cell-impermeable $PLA_2$ inhibitors that interfere with the action of the different $sPLA_2$s at the cell membrane, but do not enter the cell, as has long been proposed. Extracellular $PLA_2$ inhibitors protect the cell membrane from pro-inflammatory agents through their lipid moiety, which incorporates into the cell membrane and suppresses the activation of endogenous $sPLA_2$. An excellent review of $PLA_2$ inhibitors is provided by J. Balsinda, et al., Annu.Rev. Pharmacol. Toxicol. 39 (1999) 175–189, the contents of which are incorporated by reference herein.

The applicants have, through cloning and expression, shown that the PLI termed phospholipase inhibitor from python (PIP) possesses potent non species-specific antitoxic and anti-inflammatory activities, which have been linked to its ability to inhibit $sPLA_2$. This inhibitor signifies structural homology with other c-type snake PLIs and various mammalian proteins belonging to the 'three fingers' neurotoxin superfamily, including the urokinase-type plasminogen-activator receptor, membrane proteins of the Ly-6 family, and a bone-specific protein RoBo-1. On the basis of sequence homology study, it has been possible to identify short peptides that act as a surrogate for the larger molecule and find use as potential anti-inflammatory agents. Recently, the importance of proline brackets flanking protein-protein interaction sites has been emphasized in identifying potential functional sites in proteins. Applicants have exploited this hypothesis to identify the active site on PIP that binds to s $PLA_2$s potently in a non-species-specific manner.

Secretory and cytosolic $PLA_2$s are known to be involved in the generation of arachadonic acid metabolites. Inhibition of sPLA and cPLA can reduce or prevent the deleterious effects of an inflammatory response and neuronal degeneration by down-regulating secondary inflammatory mediators. The applicants have in their earlier work, analysed a $PLA_2$ inhibitor termed Phospholipase Inhibitor peptide from Python or PIP which is subject of the PCT Application No. PCT/SG00/00201, the contents of which in its entirety is incorporated by reference herein. Homology searches in the databases with other structurally similar snake $PLA_2$ inhibitors which have sequence identities around 60% and whose matches satisfy the pre-set E-value of 0.001 were conducted. It became apparent that proline residue was conserved amongst most of the PLAs searched. Peptides representing short homologous regions that are located on either side of a proline residue, of the snake Phospholipase inhibitors (PLIs) were synthesized and analysed for $PLA_2$ inhibitory activity. A 17-residue peptide segment of PIP, named P-NT.II (56–72 residues) that has no proline present within or on either side of this particular segment was examined along with a family of peptides representing various regions (i.e., N-terminal, middle and C-terminal) of PIP for comparison (Table 2). The presence of a cluster of hydrophobic residues within its sequence and the fact that this segment appears to be less conserved amongst the members of the snake PLI family, prompted further investigations in designing this $PLA_2$-inhibitory peptide. The minimum length of the PIP amino acid sequence that had $PLA_2$-inhibitory property was also determined. Some amino-acid substitutions were engineered and their results on $PLA_2$-inhibitory effect analysed. It was seen that 59–67 residue fragment (SEQ ID NO. 8) had high inhibitory effect on $PLA_2$ levels. However, when the same molecule was dimerised (SEQ ID NO. 9), the inhibitory effect improved dramatically. Also substitution of Aspartic acid to Glutamic acid in a derivative molecule of SEQ ID NO. 8 seemed to enhance its PLI activity. The peptides with surprisingly superior $PLA_2$ inhibitory values were evaluated for their biological effects, namely in reducing inflammatory damages both using cell lines and a transgenic mouse model prone to recurrent inflammatory polyarthritis. Their neuro-protective effect, again mediated via $PLA_2$-inhibition was investigated on hippocampal tissue sections leading to the $PLA_2$-inhibitory peptides of the current invention.

The applicants have earlier isolated PIP, purified it by sequential chromatography and cloned to elucidate its primary structure and fundamental biochemical characteristics. A cDNA clone encoding PIP was isolated from the liver total RNA by reverse transcriptase-polymerase chain reaction (RT-PCR). It contained a 603 bp open reading frame that encoded a 19-residue signal sequence and a 182-residue protein. PIP showed about 60% sequence homology with those $PLA_2$ inhibitors having a urokinase-type plasminogen activator receptor-like domain structure. PIP was also functionally expressed as a fusion protein in *Escherichia coli* to explore its potential therapeutic significance. The recombinant PIP was shown to be identical to the native form in chromatographic behavior and biochemical characteristics. Both the native and recombinant PIP appear to exist as a hexamer of 23-kDa subunits having an apparent molecular mass of ~140 kDa. PIP showed ability to bind to the major $PLA_2$ toxin (daboiatoxin, DbTx) of Daboia russelli siamensis at 1–2-fold molar excess of inhibitor to toxin. It exhibited a broad spectrum in neutralizing the toxicity of various snake venoms and toxins and inhibited the formation of edema in mice. Cloning and expression of recombinant PIP is described by Thwin et al. in Biochem. (2000), 39 9604–11, the contents of which in their entirety are incorporated by reference herein. The results confirm the venom neutralizing potential of the recombinant PIP and suggest that the proline-rich hydrophobic core region may play a role in binding to $PLA_2$.

PLI peptides may be generated by any known method in the arts. It is preferable to synthesize it by conventional solid-phase chemistry. The method involving 9-fluorenylmethoxy carbonyl chemistry may be used to synthesize the peptides. Since the peptides are short stretches, these may be more amenable to synthesis using peptide synthesizers.

Alternatively, these may be produced by recombinant methods wherein corresponding polynucleotide sequences may be cloned and expressed using suitable expression vectors known to practitioners in the art. *E. coli* for example may be used as a preferable expression system to produce the peptide by recombinant means. These peptides may be sequentially purified by chromatography and gel filtration techniques to yield pure quantities of the peptides.

The peptides may be tested for biological activity specifically pertaining to PLA inhibition. Binding assays to various isoforms of PLA may be conducted to evaluate potential of the peptides for therapeutic or prophylactic intervention. Similarly, competitive inhibition assays may be employed to assess the viability of these peptides for inhibition of PLA.

Peptides that have sequence homologies to the PLA inhibitory peptides described in the invention and may have potential as anti-inflammatory, anti-cancer or neuroprotective agents may be identified using polypeptides that bind to the peptides disclosed herein. These may be achieved by generating monoclonal or polyclonal antibodies against these peptides and using them for screening assays. Monoclonal antibodies may be generated by immunizing an animal with the peptide, then collecting its splenocytes, specifically B cells. These antibody secreting B cells are fused with myeloma cells to immortalize them. The resulting hybridoma is cultured and secretes antibodies which are characterized for reactivity to the peptide. Small peptides or hapten molecules may be conjugated to larger carrier molecules before immunization to elicit an immune response. Antibodies with high specificities may be used to screen other PLI molecules having similar epitopes as the immunizing peptide.

Pharmaceutical compositions may be used to deliver the PLI peptides in vivo. The peptides may either be delivered singly or as a cocktail of peptides having high $PLA_2$ inhibitory values. These compositions may include permissible carriers, diluents and excipients. Methods of sustained release involving nanoparticles or biodegradable polymers encapsulating the peptides are also envisaged. While selecting the composition or vehicle for delivering the peptide, care must be exercised that the peptides are not denatured or their bioactivity inhibited by the nature of the carrier.

The PLA inhibitory peptides may be administered by injection, topical application, or orally administered. Intramuscular, intraperitoneal or sytemic administration may be employed to deliver the peptides to a subject. Systemic administration may be provided by either a single injection or a series of spaced multiple injections. Alternatively, they may be amenable to administer passively through absorption through the skin such as through dermal patches. A preferred route for administration would be the oral route. Particulate material preferably biologically inert may be employed for adsorbing the peptide for oral administration. They may be incorporated into edible material to facilitate oral administration.

The dosage of composition containing the peptide may be determined by a host of factors. These may include the species which is subjected to administration, the body weight of the subject, the biological effect such as the extent of modulation of PLA activity that is desired etc. Dosage may also be based on therapeutic or prophylactic nature of intervention desired. Dosage is stated as the active amount of the inhibitory peptide in the pharmaceutical composition administered. Based on extrapolation of mouse data it was determined that for a human with a body weight of 70 Kilograms, the dose range sufficient to elicit neuro-protective or anti-inflammatory response may be 50 mg-1 g, more preferably between 120–150 mg and most preferably between 100–130 mg per subject. The injections may preferably be given as a series of five injections.

Also envisaged are the use, of plasticizers, pharmaceutical excipients, other soluble peptides, diluents, carriers, stabilisers, binders, lubricants, glidants, colouring agents, flavours and combinations thereof.

The invention will be better understood from the reading of the following non-limiting examples, which are provided only for illustrative purposes.

EXAMPLE I

Synthesis of Peptides

All peptides were synthesized by the solid phase method using 9-fluorenylmethoxy carbonyl chemistry. The synthesized peptides were purified by successive chromatography with gel filtration and reverse phase-HPLC to more than 95% purity. Yields in the range between 10–30% were obtained. The amino acid sequences of the peptides so obtained were validated by matrix assisted laser desorption/ionization time-of-flight mass spectrometry (MALDI-TOF-MS).

EXAMPLE II

Comparison of $PLA_2$-Inhibitory Activity

The phospholipase $A_2$ inhibitory activity of the various peptides against the snake venom $PLA_2$ (crotoxin B) and other types of $PLA_2$s was evaluated in vitro using labeled *E. coli* membranes as substrate according to the method described in *Eur. J. Biochem.* 269, 719–727 (2002), the entire contents of which are incorporated by reference herein.

TABLE 1

Properties and inhibitory data of peptides derived from various PIP segments

| No. | Code | Sequence | Mol. Wt. (Mr) | Length (residue) | *$IC_{50}$ ($\mu$M) |
|---|---|---|---|---|---|
| 1. | P-NT.I A | $^{10}$GDDCDGYQEECPS$^{22}$ | 1417.0 | 13 | 41.8 |
| 2. | P-NT.I B | $^{22}$SPEDRCGKILIDIALA$^{37}$ | 1714.0 | 16 | 9.4 |
| 3. | P-NT.II | $^{56}$LGRVDIHVWDGVYIRGR$^{72}$ | 2011.3 | 17 | 4.9 |
| 4. | P-PB.I | $^{86}$LPGLPLSLQNGLY$^{98}$ | 1384.6 | 13 | 37.8 |

TABLE 1-continued

| Properties and inhibitory data of peptides derived from various PIP segments | | | | | |
|---|---|---|---|---|---|
| No. | Code | Sequence | Mol. Wt. (Mr) | Length (residue) | *$IC_{50}$ ($\mu$M) |
| 5. | P-M.I | $^{101}$GAFGIFTEDSTEHEV$^{115}$ | 1638.7 | 15 | 54.7 |
| 6. | P-CT.I | $^{137}$GNITYNIKGCVSS$^{149}$ | 1355.5 | 13 | 43.2 |
| 7. | P-CT.II | $^{151}$PLVTLSERGHEGRKN$^{165}$ | 1692.9 | 15 | 49.6 |
| 8. | Scrambled P-NT.II | YRRVDIGLRVWHDLGVG | 2011.3 | 17 | >>250 |

$IC_{50}$ values were calculated from the corresponding dose-response curves by nonlinear regression analysis using GraphPad Prism (version 2.01).

Table 1 shows the amino acid sequences and properties of peptides derived from various regions of PIP (FIG. 1), along with the inhibitory data obtained from in vitro inhibition experiments. As judged by $IC_{50}$ values, the peptide P-NT.II among those examined was found to be the most effective inhibitor against the snake venom $sPLA_2$ (crotoxin subunit B). With an $IC_{50}$ ranging from 3.9–4.9 µM, P-NT.II was found to be an effective inhibitor not only for snake venom $sPLA_2$s, but also for human type II $sPLA_2$.

Figure 2:
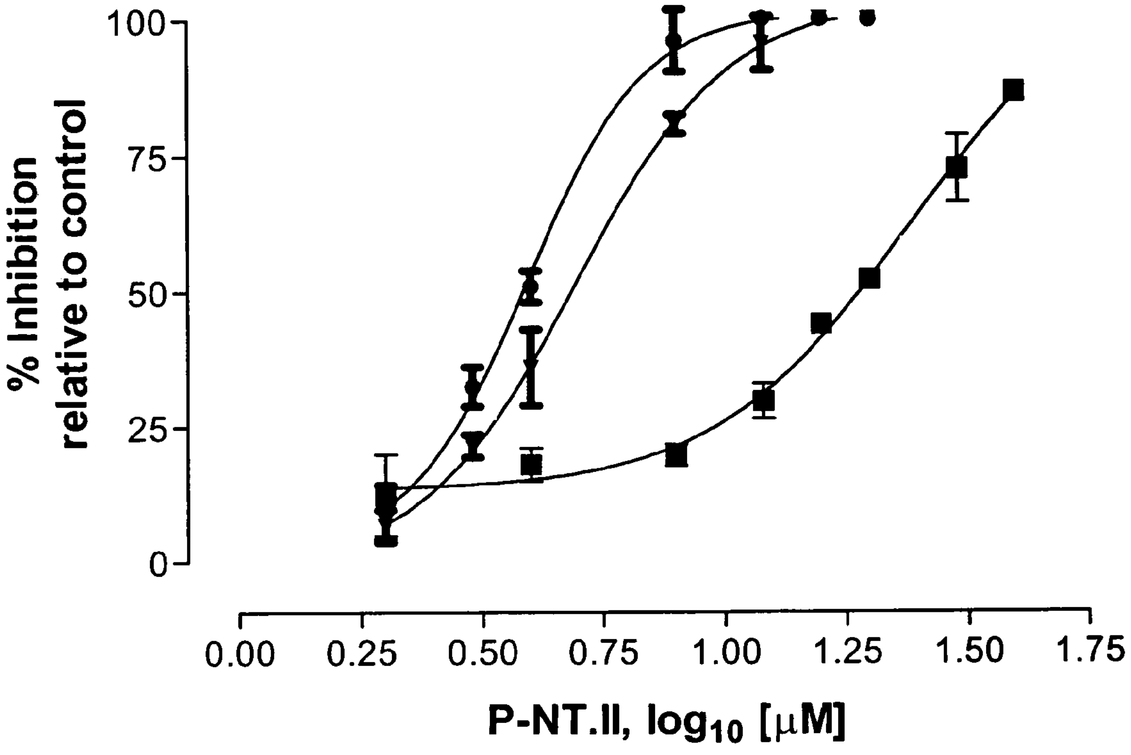
FIG. 2 shows $PLA_2$ inhibition profiles of the active peptide P-NT.II against enzymatic activity of various other $PLA_2$s in *E. coli*-membrane assay.

The active peptide (P-NT.II) dose-dependently inhibited the catalytic activity of the $PLA_2$ isoforms over a wide concentration range (1–250 µM) (FIG. 2). The $IC_{50}$ values (mean±SD; n=3) determined from the inhibition profiles by nonlinear regression analyses were, 4.91±2.47, 3.91±1.67 and 23.91±2.39 µM for CB (snake type IIA $sPLA_2$), arthritis synovial fluid (human type IIA $sPLA_2$), and a 100-kDa human recombinant cytosolic form of $PLA_2$ ($cPLA_2$), respectively. At 6 and 10 µM concentrations, P-NT.II selectively and efficiently inhibited 80 and 90%, respectively of $sPLA_2$ activity, while 12-epi-sclaradial, a known $sPLA_2$ inhibitor used as a positive control, inhibited 75 and 95% of $sPLA_2$ activity, respectively at 10 and 20 µM concentrations. These results indicate the usefulness of P-NT.II as a selective and effective inhibitor of $sPLA_2$ over $cPLA_2$.

Binding Assays:

Experimental evidence for the direct binding of the active peptide P-NT.II to both $sPLA_2$ and $cPLA_2$ isoforms was demonstrated by ELISA using biotinylated-P-NT.II FIGS. 3A and 3B). The purity of the biotinylated P-NT.II as evaluated by RP-HPLC was 96%, and the mass ($M_r$) was determined to be 2114.98. Based on the mass of the intact peptide ($M_r$=2011.33) and that of the biotinylated product, 0.18 mol biotin was apparently bound to 1 mol of P-NT.II. All the venom $sPLA_2$s representing three groups —β-bungarotoxin (Group I), crotoxin B (Group IIA) and bee (*Apis mellifera*) venom $PLA_2$ (Group III)—and the human recombinant $cPLA_2$, reacted positively with the biotinylated-P-NT.II. In addition, the peptide was also found to inhibit another isoform—$cPLA_2$, although it showed a five-fold selectivity for the former over the latter. Although the biotinylated P-NT.II also binds to $cPLA_2$, its binding is relatively much weaker than that seen with the $sPLA_2$s, indicating the selectivity of P-NT.II peptide binding to $sPLA_2$ over $cPLA_2$ (FIG. 3A). The fact that binding between the labeled peptide and mammalian (human and rat) type IIA $sPLA_2$ (FIG. 3B) was inhibited by 15 µM unlabeled (native) peptide indicates that the native P-NT.II could compete with the labeled P-NT.II. A synthetic peptide derived from the scrambled sequence of P-NT.II, failed to inhibit both $sPLA_2$ and $cPLA_2$. These results demonstrate the specific binding between the peptide P-NT.II and type IIA $sPLA_2$s of mammalian origin and snake venom.

EXAMPLE III

Optimising P-NT.II Peptide

With the aim of optimising the $sPLA_2$-inhibitory potency of P-NT.II, a number of P-NT.II analogs were synthesized using solid phase chemistry to make suitable changes in the amino acid sequence of P-NT.II (Table 2). Based on in vitro inhibition assays against a purified human synovial $sPLA_2$ (Cayman, USA), P-NT.II anlog PIP(59–67) was identified as the shortest peptide possessing strongest $sPLA_2$-inhibitory activity ($IC_{50}$ 3.8).

Displacing Asp (D) with Ala (A), Ser (S) or Glu (E) did not significantly enhance the inhibitory potency However, dimerization of PIP (59–67) resulted in significant enhancement in $sPLA_2$ inhibitory activity, with its potency ($IC_{50}$ 1.19) found to be equal to or higher than that (FIG. 14) of the indole analog LY315920 ($IC_{50}$ 2.29), which was the first potent and selective $sPLA_2$ inhibitor (Eli Lilly Research Laboratories, USA). This LY315920 analog is a selective inhibitor of group IIA secretory phospholipase $A_2$ (*J Pharmacol Exp Ther.* 1999; 288(3):1117–24) that has recently been shown to inhibit serum group IIA secretory phospholipase $A_2$ enzyme activity in patients with severe sepsis in a multicenter, double-blind, placebo-controlled clinical trial (*Crit Care Med.* 2003; 31(3):718–28).

TABLE 2

Inhibitory potency of various peptide analogs against Group IIA purified human synovial $sPLA_2$

| # | Peptide Analog (residue No.) | Sequence | M.W. | Mean % Inhibition* | $IC_{50}$ [μM]″ |
|---|---|---|---|---|---|
| 1 | P-NT.II (56–72) | LGRVDIHVWDGVYIRGR | 2011 | 55.61 | 5.30 |
| 2 | PIP (56–67) | LGRVDIHVWDGV | 1365 | 34.21 | — |
| 3 | PIP (57–67) | GRVDIHVWDGV | 1252 | 14.22 | — |
| 4 | PIP (58–67) | RVDIHVWDGV | 1195 | 59.47 | 3.67 |
| 5 | PIP (59–67) | VDIHVWDGV | 1039 | 56.37 | 3.80 |
| 6 | PIP (60–67) | DIHVWDGV | 940 | 45.85 | 5.75 |
| 7 | PIP (61–67) | IHVWDGV | 825 | n.s. | — |
| 8 | PIP (62–66) | HVWDG | 613 | n.s. | — |
| 9 | PIP (61–66) | IHVWDG | 726 | n.s. | — |
| 10 | PIP (60–66) | DIHVWDG | 841 | n.s. | — |
| 11 | D65A-PIP (59–67) | VDIHVW**A**GV | 995 | 48.52 | 5.45 |
| 12 | D65S-PIP (59–67) | VDIHVWSGV | 1011 | 52.55 | 5.25 |
| 13 | D65E-PIP (59–67) | VDIHVW**E**GV | 1053 | 57.62 | 4.95 |
| 14 | D60, 65E-PIP (59–67) | V**E**IHVW**E**GV | 1067 | 61.42 | 4.20 |
| 15 | PIP (59–67) dimer | VDIHVWDGV VDIHVWDGV | 2060 | 74.55 | 1.19 |

*Mean % inhibition at fixed peptide concentration [5 μM].
″As assayed using $^3$H-LabeLled *E. coli* membranes as substrate (estimated $IC_{50}$ values may vary depending on the type of method used for measuring the $PLA_2$ activity).

It was observed that the minimal sequence required for having $PLA_2$-inhibitory activity from the PIP sequence was the 59–67 residue peptide as shown by the percentage inhibition and $IC_{50}$ values. However, amino acid substitutions to this sequence did not significantly change its $PLA_2$-inhibitory properties. It was seen that dimerising the 59–67 residue peptide significantly increased its inhibitory effect. However, the most potent of these inhibitory peptides was P-NT.II which had both higher inhibitory potential and $IC_{50}$ value. Clinical evaluations were all conducted with this peptide.

The utility of the peptides as a prophylactic agent for modulating inflammatory diseases such as rheumatoid arthritis, was investigated through its therapeutic and/or prophylactic effectiveness in modulating joint inflammation in Tg197 transgenic mice that spontaneously develop chronic inflammatory polyarthritis under untreated conditions. Treatment of these arthritic mice, particularly the males, with the candidate peptide P-NT.II indeed modulates the disease as confirmed by histopathological evaluations.

EXAMPLE IV

Transgenic Mouse Model for Anti-Inflammatory Response

P-NT.II was investigated as a prophylactic agent for modulation of inflammatory disease such as rheumatoid arthritis by its therapeutic and/or prophylactic effectiveness in modulating joint inflammation in Tg197 transgenic.

The candidate peptide P-NT.II was dissolved in dimethyl sulfoxide (DMSO) at a final concentration of 3 mg/mL. Two sets of experiments were conducted. In Experiment 1 (n=28 Transgenic (Tg197)+7 wild type (wt), peptide-treated animals (Group B) received intra-peritoneal (i.p) injections of 10 mg/kg, thrice weekly for 5 consecutive weeks, while the vehicle controls (Group E) were injected with DMSO (3 mL/kg) only. Non-transgenic (wild type) mice in different groups (C, D) were similarly treated either with the same i.p dose of peptide or DMSO. At the end of the experiment following 5 weeks of peptide injection, each Tg197 mice received a total dose of 1.8 mg of peptide P-NT.II (0.9 μmole).

In experiment 2, mice were divided into 6 groups (A–F), and were injected i.p with 3 weekly doses (150 μg peptide in 50 μL DMSO per dose) of either the test peptide P-NT.II or the control peptide with the scrambled sequence for 4 consecutive weeks. Tg197 mice in Group B (n=18) were further divided into 4 sub-groups ($B_1$, $B_2$, $B_3$, $B_4$). At the end of 1$^{st}$ week, four Tg197 mice from Group B (sub-group $B_1$) were sacrificed and both hind legs taken for histological processing and scorings. The remaining Tg197 mice from the other sub-groups B were continued with 3 regular doses of injections per week, and four Tg197 mice from each sub-group $B_2$ and $B_3$, were sacrificed at the end of 2$^{nd}$ and 3$^{rd}$ weeks, respectively. At the end of 4$^{th}$ week, all remaining Tg197 mice (n=8) were sacrificed for collection of joint specimens.

Grading of Disease

Disease monitoring was done by gross observations based on body weight measurements and arthritis scoring, which were done twice weekly after treatment until all the animals were sacrificed at 5$^{th}$ week in experiment 1, or at 4$^{th}$ week in experiment 2. Arthritis score (AS) was recorded on both ankle joints, and average scores as shown below were taken:

0=no arthritis (normal appearance and flexion);

0.5=onset of arthritis (mild joint swelling);

1.0=mild arthritis (joint distortion);

1.5=as above+finger deformation, less strength on flexion;

1.1=moderate arthritis (severe swelling, joint deformation, no strength on flexion);

2.5=as above+finger deformation in paws;

3.0=heavy arthritis (ankylosis detected on flexion and severely impaired movement).

For histopathological scoring, both hind legs were dissected and fixed in 10% formaldehyde overnight, decalcified in citrate-buffered formic acid for 3 days at 4° C., and processed for light microscopy (LM).

Histopathological score (HS) was evaluated as follows:

0=no detectable pathology,

1=hyperplasia of the synovial membrane and presence of polymorphonuclear infiltrates 2=pannus and fibrous tissue formation and focal subchondrial bone erosion 3=articular cartilage destruction and bone erosion 4=articular cartilage destruction and extensive bone erosion.

EXAMPLE V

Ultrastructure Studies

Transmission electron microscopy (TEM): Ankle joints dissected from the left hind leg of each mouse were split open longitudinally through the midline between the tibia and the talus, prefixed overnight with 2.5% glutaraldehyde in phosphate buffer, pH 7.4 (PB) and rinsed with PB. After fixing with 1% osmium tetroxide in PB for 2 h, they were dehydrated in a graded series of ethanol and processed into Araldite. Semi-thin sections (1.0μ) were cut and stained with methylene blue to observe the orientation and for histopathological scorings under the light microscope. Ultra-thin sections (80–90 nm) were then cut with an ultramicrotome (Riechert-Jung Ultracut E), mounted on copper grids, counterstained with uranyl acetate and lead citrate, and evaluated under electron microscope (CM120 Biotwin, FEI Company).

Anti-inflammatory activity of the candidate peptide P-NT.II was examined as a new treatment option for modulating rheumatoid arthritis (RA) in a transgenic animal model. To evaluate the potential effectiveness of the peptide as prophylaxis against RA, two separate experiments were performed in 4 week-old transgenic (Tg197) mice and non-transgenic wild-type (wt) mice. These transgenic mice (Tg197) express human tumor necrosis factor (TNFα), a cytokine which has been implicated in the pathogenesis of human RA. The animals exhibit severe chronic arthritis of the fore and hind paws at 4–5 weeks after birth, which can be detected by gross observation and histological analyses.

TABLE 3

Histological scores of Tg197 mice before and 5 week post-treatment with P-NT.II or DMSO.

| Treatment | Tg197 Mice | Joints Scored | % of total at indicated HS scores HS 2 | HS 3 | HS 4 | Mean HS ± SEM |
|---|---|---|---|---|---|---|
| Untreated | 4 M | 8 | 0 | 62.5 | 37.5 | 3.44 ± 0.17 |
| | 4 M + 4 F | 16 | 0 | 62.5 | 37.5 | 3.47 ± 0.12 |
| +P-NT.II | 4 M | 8 | 62.5 | 37.5 | 0 | 2.37 ± 0.18 |
| | 4 M + 3 F | 14 | 35.7 | 64.3 | 0 | 2.71 ± 0.15 |
| +DMSO | 3 M | 6 | 0 | 83.3 | 16.7 | 3.33 ± 0.17 |
| | 3 M + 3 F | 12 | 8.3 | 75.0 | 16.7 | 3.25 ± 0.13 |

TABLE 4

Histological scores of Tg197 mice before and 4 week post-treatment with P-NT.II or control scrambled peptide

| Treatment | Tg197 Mice | Joints Scored | % of total at indicated HS scores HS 2 | HS 3 | HS 4 | Mean HS ± SEM |
|---|---|---|---|---|---|---|
| Untreated (4 wk) | 7 M + 3 F | 10 | 0 | 90.0 | 10 | 3.30 ± 0.11 |
| +P-NT.II (1 wk) | 3 M + 1 F | 4 | 100 | 0 | 0 | 2.12 ± 0.12 |
| +P-NT.II (2 wk) | 3 M + 1 F | 4 | 100 | 0 | 0 | 2.37 ± 0.12 |
| +P-NT.II (3 wk) | 2 M + 2 F | 4 | 75 | 25 | 0 | 2.50 ± 0.20 |
| +P-NT.II (4 wk) | 3 M + 1 F | 4 | 75 | 25 | 0 | 2.62 ± 0.31 |
| +Scrambled peptide (4 wk) | 4 M + 2 F | 6 | 16.7 | 83.3 | 0 | 3.25 ± 0.17 |

HS = 2 (very mild arthritis with minimal inflammation);
HS = 3 (moderate arthritis with inflammatory cells and signs of bone and cartilage erosions);
HS = 4 (severe arthritis with maximal inflammation and complete loss of bone architecture).

FIGS. 6A to 6F illustrate the histological features of Tg197 mice before and after treatment with the peptide P-NT.II. Histologically, 100% of the joints from the untreated group were moderately (62.5% in experiment I, and 90% in experiment II) to severely (37.5% and 10% in experiments I and II, respectively) damaged by the expansion of the synovial pannus, fibrin exudate and mononuclear cells, which accumulate in the synovial space. (FIGS. 6A, B; Tables 3, 4). Not a single joint (0%) of those untreated mice in both experiments, had normal or minimal signs of inflammation. In contrast, 35.7% of joints from mice treated with the peptide P-NT.II had almost normal synovial membrane architecture with minimal signs of inflammation and a negligible accumulation of inflammatory cells in experiment I. Even better therapeutic effectiveness was evident in experiment 2, in which 100% and 75% of the joints of peptide-treated mice were either normal or only mildly affected by arthritis in the first two weeks and in the last two weeks, respectively after peptide treatment (FIG. 6C, D). On the other hand, the joints of mice treated with either DMSO or the control scrambled peptide had histological features similar to those of the untreated mice, with most joints (8%) showing signs of mild to severe inflammation (Table 3). These results are indicative of the powerful suppressive effect of this therapeutic approach on inflammatory process.

FIGS. 7A to 7C show the histograms and statistical analyses made for overall histological evaluation, with scores assigned for erosion of all joints from mice treated with the test peptide for 5 weeks in the first experiment, and for 4 weeks in the second experiment. In experiment 1, the peptide-treated group had significantly lower histological scores ($P<0.05$) when compared with untreated or DMSO-treated mice (n=4 males+4 females/group). One-way ANOVA with Bonferroni's multiple comparison test (FIG. 7A) shows significant difference between the selected groups ($P<0.001$ for peptide treated vs untreated groups; $P<0.01$ for peptide treated vs DMSO-treated groups). In male Tg197 mice (FIG. 7B), the effectiveness of the peptide was more pronounced as indicated by significantly lower histological scores for peptide-treated group as compared with untreated or DMSO-treated groups ($P<0.001$ for both cases). In females (FIG. 7C), the effect of peptide on joint damage was less evident ($P>0.05$), as the females in the tested colonies were much weaker than the males and hence more susceptible to the disease.

In the second experiment, the histological scorings of Tg197 mice taken with time course at pre- and 4 week post-treatment with the test peptide P-NT.II indicate that treatment with the test peptide significantly reduced HS of the experimental groups (1–4 weeks) as compared to untreated or scrambled peptide treated group (FIG. 8). These results demonstrate suppression of articular cartilage and bone erosion by treatment with the candidate peptide P-NT.II, particularly in the male transgenic Tg197 mice, and suggest a crucial role for secretory phospholipase $A_2$ inhibitors in the mediation of joint inflammation in rheumatoid arthritis.

Gross observations based on arthritis scores (AS) of the ankle joints of untreated Tg197 mice and those treated with the peptide P-NT.II or vehicle DMSO are shown in Table 5.

TABLE 5

Arthritis scores (AS) of Tg197 mice at pre- and 5 week post-treatment with P-NT.II or DMSO.

| Treatment | Tg197 Mice | Joints Scored | % of total joints AS (1) | AS (1.5–2) |
|---|---|---|---|---|
| Untreated | 4 M | 8 | 0 | 100 |
| | 4 M + 4 F | 16 | 0 | 100 |
| +P-NT.II | 4 M | 8 | 87 | 13 |
| | 4 M + 3 F | 14 | 50 | 50 |
| +DMSO | 3 M | 6 | 50 | 50 |
| | 3 M + 3 F | 12 | 33 | 67 |

AS 1 = mild arthritis (joint distortion);
AS 1.5 = mild arthritis + finger deformation and less strength on flexion According to gross observations on the basis of AS, 100% of ankle joints (n=16) of the untreated mice (4 males+4 females) had mild arthritis with obvious finger deformation and less strength on flexion (AS=1.5). In contrast, only 50% of the joints (n=14) of peptide-treated mice (4 M+3 F) had a similar AS of 1.5, while those (3 M+3 F) treated with the vehicle alone (DMSO) had 67% of the joints (n=12) affected by the same degree of arthritis. In the males, the modulatory effect on arthritis was even more pronounced as evidenced by a mere 13% of the ankle joints affected by arthritis with an AS of 1.5, as compared to 100% detected in the untreated and 50% in the DMSO-treated mice.

Besides these clinical and histologic assessments, morphological evaluations at the cellular level in the articular cartilage and synovium of the ankle joints of TNF transgenic were also made before and after treatment with the anti-inflammatory peptide P-NT.II. At 1–4 weeks post-treatment with the peptide P-NT.II, the number of inflammatory cells in the synovium was reduced as early as 1 week after initiation of treatment, and the structural organization of the synovial membrane of the ankle joint appeared less modified 4 weeks after the treatment. Lesions such as cell fragmentations due to degeneration of synoviocytes and dilation of the rough endoplasmic reticulum (FIG. 9A), and synovial adhesions (FIG. 9B) were less obvious in the peptide-treated mice (FIG. 9C) as compared to those changes seen in the untreated or scrambled P-NT.II-treated (negative control) groups. The beneficial effect of the peptide was also evident in the articular cartilage at 1–4 weeks post-treatment FIGS. 10A to 10G). In the joints of peptide-treated Tg197 mice, the ultrastructural features of the articular chondrocytes did not significantly differ from those seen in the joints of normal wildtype mice. Most of them had prominent nucleus, lined by plasma membrane with short cytoplasmic protrusions, and vacuoles, rough endoplasmic reticulum and mitochondria in the cytoplasm (FIG. 10A). In contrast, the ultrastructure of chondrocytes of Tg 197 mice at 4 weeks post-treatment with the negative control peptide (scrambled P-NT.II) was more or less similar to those described for untreated Tg197 mice showing degenerating features such as a greatly vacuolated cytoplasm and pycnotic nuclei (FIG. 10B) or loss of nucleus with disrupted rough endoplasmic reticulum (FIG. 10C). Ultrastructural features of the articular cartilage observed in this human TNF transgenic mouse model of rheumatoid arthritis (RA) suggest that the chondrocyte may be one of the important targets of the peptide intervention in modulating the progression of the joint erosion. Extensive histopathologic analysis of joints in the Tg 197 TNF model revealed that in contrast to massive cartilage and subchondral bone erosion usually seen in untreated transgenic Tg197 mice, P-NT.II significantly reduced chondrocyte necrobiosis as well as bone erosions in the peptide-treated mice (FIG. 11). Statistical analysis revealed a greater beneficial effect of P-NT.II on cartilage destruction and bone erosion (**$P<0.01$ versus untreated or scrambled P-NT.II-treated groups for both parameters) than on synovitis (*$P<0.05$ versus untreated or scrambled P-NT.II-treated groups). Since prevention of bone and cartilage destruction is critical in the treatment of inflammatory bone loss disease such as RA, the bone and cartilage protective effect of the peptides P-NT.II may offer advantage over conventional drugs which fall short of achieving this goal.

In a time-course study to evaluate the specific effect of peptide in modulating the serum $sPLA_2$ levels in Tg197 mice (FIG. 12), P-NT.II significantly suppressed the circulating $sPLA_2$ at 3–4 weeks post-treatment ($P<0.05$), when compared with the serum levels of the untreated mice. In contrast, the circulating $sPLA_2$ of scrambled P-NT.II-treated and untreated Tg197 mice for the corresponding period were not significantly different ($P>0.05$) thus indicating the specific effect of the peptide P-NT.II on $sPLA_2$ levels. Elevated levels of $sPLA_2$ had been reported in the plasma of patients with acute and chronic inflammatory diseases by several investigators (*Scand J Rheumatol* 1994; 23:68–72; *Circ Shock* 1993; 39:160–7; *Gut* 1993; 34:1133–36). The results obtained from P-NT.II-treated Tg197 mice demonstrated that this new peptide inhibitor significantly suppressed the circulating $sPLA_2$ activity in those mice, whereas scrambled P-NT.II (negative control peptide) was without any effect. P-NT.II might modulate ultrastructural modifications to the synovium and articular cartilage by reducing arachidonic acid (AA) bioavailability through $sPLA_2$ inhibition, and thus suppress the severity of the PG-mediated inflammatory response.

EXAMPLE VI

Cell Culture

Cell culture experiments employing mouse macrophages were carried out in which the ability of P-NT.II to dose-dependently inhibit LPS- or TNF-induced $PGE_2$ production, was assessed (FIGS. 13A and 13B).

The murine macrophage cell line J774 (ATCC, USA) was cultured at 37° C. in humidified 5% $CO_2$/95% air in Dulbecco's Modified Eagle's Medium (DMEM) containing 10% foetal bovine serum, 2 mM glutamine, 20 mM Hepes, 100 Ul/ml penicillin and 100 μg/ml streptomycin. After growing to confluence, the cells were dislodged by scrapping, plated in 12 culture wells at a density of $5\times10^5$ cells/ml per well, and allowed to adhere for 2 h. Thereafter, the medium was replaced with fresh medium containing LPS (2 μg/ml), and either of the $PLA_2$ inhibitors (P-NT.II, scrambled P-NT.II or LY315920 (Lilly Research Laboratories, USA), dissolved in DMSO (final concentration 0.1% v/v). Peptides were tested at various concentrations ranging from 0.01–40 μM. Following incubation in 5% $CO_2$/95% air at 37° C. for 20 h, culture medium supernatants were collected and stored frozen (−80° C.) until use. In parallel experiments, cells were stimulated with mouse recombinant TNF (10 ng/ml; Sigma) for 20 h, in the presence or absence of 10 μM P-NT.II or LY315920 dissolved in DMSO (0.1% final concentration). Culture medium supernatants were collected after centrifugation (10,000 g, 4° C., 15 min) and stored at −80° C. prior to measurement of $PGE_2$, which was done according to the manufacturer's instructions (EIA kit-monoclonal, Cayman Chemical, USA).

It was observed that P-NT.II peptides could dose-dependently inhibit LPS— or TNF-induced $PGE_2$ production with a potency equalling that of another potent and selective $sPLA_2$ inhibitor—LY315920 analog (Lilly Research Laboratories, Eli Lilly & Company, Lilly Corporate Center, Ind., USA).

EXAMPLE VII

Cell Viability Assays

XTT (Sodium 3'-[Phenyl amine carboxyl)-3,4-tetrazolium]-bis(4-methoxy-nitro)benzene sulfonic acid hydrate) Cell Proliferation Kit II (Roche Applied Science) was used to assess the possible cytotoxic effect of P-NT.II on the mouse macrophage J774 cell line.

EXAMPLE VIII

Measurement of Serum Phospholipase $A_2$

Serum of transgenic (Tg197) mice and non-transgenic wild type controls were measured for $sPLA_2$ using an *Escherichia coli* (*E. coli*) membrane assay as described previously [*Eur J Biochem* 2002, 269:719–727]. In brief, [$^3$H] arachidonate-labeled *E. coli* membrane suspension (5.8 μCi/μmol, Perkin Elmer, USA) was used as substrate, and 25 mM $CaCl_2$-100 mM Tris-HCl (pH 7.5) as assay buffer. The reaction mixture containing substrate (20 μl), and either purified human synovial $sPLA_2$ standard (1–80 ng/ml, Cayman, USA) or serum (10 μl) in a final volume of 250 μl in assay buffer was incubated at 37° C. for 1 h, and the reaction terminated with 750 μl of chilled PBS containing 1% BSA. 500 μl aliquots of the supernatant were then taken to measure the amount of [$^3$H] arachidonate released from the *E. coli* membrane using liquid scintillation counting (Beckman LS 6500 Scintillation Counter). The amount of $sPLA_2$ present in the serum was calculated from the standard curve, and is expressed as ng/ml±SEM. Circulating levels of $sPLA_2$ were found to be significantly suppressed (FIG. 12) in the P-NT.II-treated transgenics as compared to untreated animals.

EXAMPLE IX

Preparation of Hippocampal Sections

Ischemic or oxidative stress and other neurodegenerative diseases do lead to neuronal death. The hippocampal tissue was subjected to kainate-induced injury and neuroprotective activity of the peptides to reduce or prevent neuronal damage was assessed. Organotypic hippocampal slice cultures were prepared according to the method as previously described in the *J. Neurosci. Methods* 37, 173–182 (1991) the contents of which in its entirety are incorporated by reference herein. The slices placed in 6-well tissue culture plates (Becton Dickinson, Franklin Lakes, N.J., USA) containing 1 ml of culture medium were maintained at 37° C., 100% humidity, and 95% air and 5% carbon dioxide atmosphere. The medium was changed after 3 days. At 7 d in vitro, the medium was replaced with 900–990 μl of serum-free culture medium and 10 μl of 12-epi-sclaradial, 100 μl of PNT-II peptide, or 10 μl of DMSO (vehicle control for 12-epi-sclaradial). The final concentrations of 12-epi-sclaradial and P-NT.II were 20 and 10 μM, respectively. 10 h later, 100 μl of the media containing inhibitors were removed, and replaced with 100 μl of stock solution of kainate (final concentration 10 μM). The cultures were fixed for 24 h on day 3 after kainate addition by immersion in a fixative containing 4% paraformaldehyde in 0.1M phosphate buffer (pH 7.4). Control slices were treated the same way as the slices above, except that 0.3% DMSO was added instead of the inhibitors and kainate. These tissue sections were subjected to immunocytochemical studies as elaborated in example X.

EXAMPLE X

Immunocytochemistry and Image Analyses

Polytetrafluoroethylene membranes were cut from the culture plate inserts and processed with the attached slices for free floating immunocytochemistry, using an affinity-purified rabbit polyclonal antibody to the AMPA receptor subunit GluR1 (Chemicon, diluted 1 μg/ml in PBS-milk powder). The slices were then washed, and reacted with an anti-rabbit secondary antibody. This was followed by three changes of PBS to remove unreacted secondary antibody. The slices were then reacted for 1 h at room temperature with an avidin-biotinylated horseradish peroxidase complex. The reaction was visualized by treatment for 5 min in 0.05% 3,3-diaminobenzidine tetrahydrochloride (DAB) solution in Tris buffer containing 0.05% hydrogen peroxide. The color reaction was stopped with several washes of Tris buffer, followed by PBS. The slices were then detached from the culture insert membranes, mounted with the immuno-reacted side-up on gelatin-coated glass slides and lightly counterstained with methyl green before coverslipping. Control sections were incubated with PBS or preimmune rabbit or mouse sera instead of primary antibody. Image analysis was carried out using the Image-Pro Plus software, version 4.1.0.0 for Windows 85/NT/98 (Media Cybernatics, Silver Spring, Md.). Images were acquired using a Zeiss Axiophot microscope fitted with a video camera. An image of the entire hippocampal slice was captured at 2.5× magnification. A curved line was then traced along the row of hippocampal pyramidal neuronal cell bodies from CA1 to CA4. This was followed by a trace, along the pyramidal neurons that showed GluR1 staining in their dendritic fields. The total length of the second trace was expressed as a percentage of the first trace. All tracings were done 'blind'. Six to twelve slices in each treatment/antibody staining category were analysed, and the results were analyzed by a two-tailed Student's t test for groups of unpaired observations. Significance was taken at $P<0.05$. The statistical significance of the effects of the peptides was also confirmed by one-way ANOVA with Dunnet's post test.

FIG. 4A shows that the hippocampal slices treated only with DMSO as a vehicle control were densely stained for GluR1 , with a row of hippocampal pyramidal neurons visibly detected. In kainate-treated slices, there was a significant decrease in the staining of pyramidal neurons (FIG. 4B) due to the death of neuronal cells caused by the neurotoxic kainic acid. Addition of PNT-II peptide (10 μM) to slices before kainate application showed a protective effect on the pyramidal cell bodies, and significantly prevented the decrease in GluR1 immunoreactivity (FIG. 4D). A similar protective effect was also seen with 12-epi-scalaradial, a known selective $sPLA_2$ inhibitor ($IC_{50}$=5.4 μM) at 20 μM (FIG. 4C). The histograms (FIG. 5) illustrates that the GluR1 immunoreactivity of pyramidal neurons is significantly ($P<0.001$) higher in the P-NT.II or 12-epi-scalaradial-treated neurons than that of the untreated cells, indicating that the $sPLA_2$ inhibitor P-NT.II is effective in preventing neuronal injury resulting from kainate treatment.

Referring now to the figures, FIG. 1 shows the alignment of the amino acid sequences of PIP with database sequences. E-value was pre-set at 0.001 for matching the amino acid sequences. The shaded boxes indicate the amino acid sequences identical to those of PIP. The boldface P represents proline. Short segments with amino acid sequences corresponding to peptide fragments—P-NT.IA, P-NT. IB, P-NT.II , P-PB.I, P-CT.I, P-CT.II—are indicated by arrows. Positions of residues used for synthesizing the peptides are shown within parentheses.

FIG. 2 shows the $PLA_2$ inhibition profiles of the active peptide P-NT.II against enzymatic activity of various sources of $PLA_2$s. Results are the mean±SD of 3 separate experiments done in triplicates. $IC_{50}$ values were graphically determined from the inhibition curves, constructed on the basis of the in vitro results of [$^3$H]-labelled *E. coli* membrane assays.

FIGS. 3A and 3B show the ELISA reactions between biotinylated P-NT.II and different sources of $PLA_2$s coated on microtitre plate wells. Biotinylated P-NT.II was directed against (A) human recombinant $cPLA_2$, venom $sPLA_2$s. β-bungarotoxin, crotoxin B, bee venom $PLA_2$ or (B) $sPLA_2$s representing mammalian type IIA. Binding was inhibited by 15 μM unlabeled (native) peptide showing that it could compete with the labeled P-NT.II. In contrast, unlabeled scrambled peptide failed to block the binding of labeled P-NT.II to immobilized $sPLA_2$s showing specific binding between the peptide P-NT.II and typeT IIA $sPLA_2$s of mammalian origin and snake venom.

FIGS. 4A to 4D illustrate the sections stained for the AMPA receptor subunit $GluR_1$, used as a neuronal marker. Normal control slices were densely stained for $GluR_1$, and hippocampal pyramidal neurons are easily visualised. In kainate-treated slices, there was a significant decrease in the staining. Addition of PNT-II peptide to slices before kainate application was protective, and prevented the decrease in GluR1 immunoreactivity after kainate treatment. 12-epi-scalaradial showed a similar protective effect.

FIG. 5 shows histograms depicting the effect of inhibitors on kainate-induced hippocampal lesions in slice culture. Hippocampal slices in culture were pretreated with either P-NT.II or 12-epi-scalaradial prior to addition of kainate. Y-axis indicates percentage of a line traced along the stratum pyramidale of the CA fields of the hippocampus that contains immunoreactivity to GluR1. Treatment of slices: C, control slices treated with DMSO, a vehicle for dissolving 12-epi-sclaradial and P-NT.II peptide; K, 100 μM kainate; S, 20 μM 12-epi-sclaradial; P, 10 μM PNT-II peptide; S+K or P+K, 20 μM 12-epi-sclaradial or 10 μM PNT-II peptide, followed by 100 μM kainate. Statistically significant differences are indicated by the P values. Error bars indicate SEM.

Figures 6, 7:
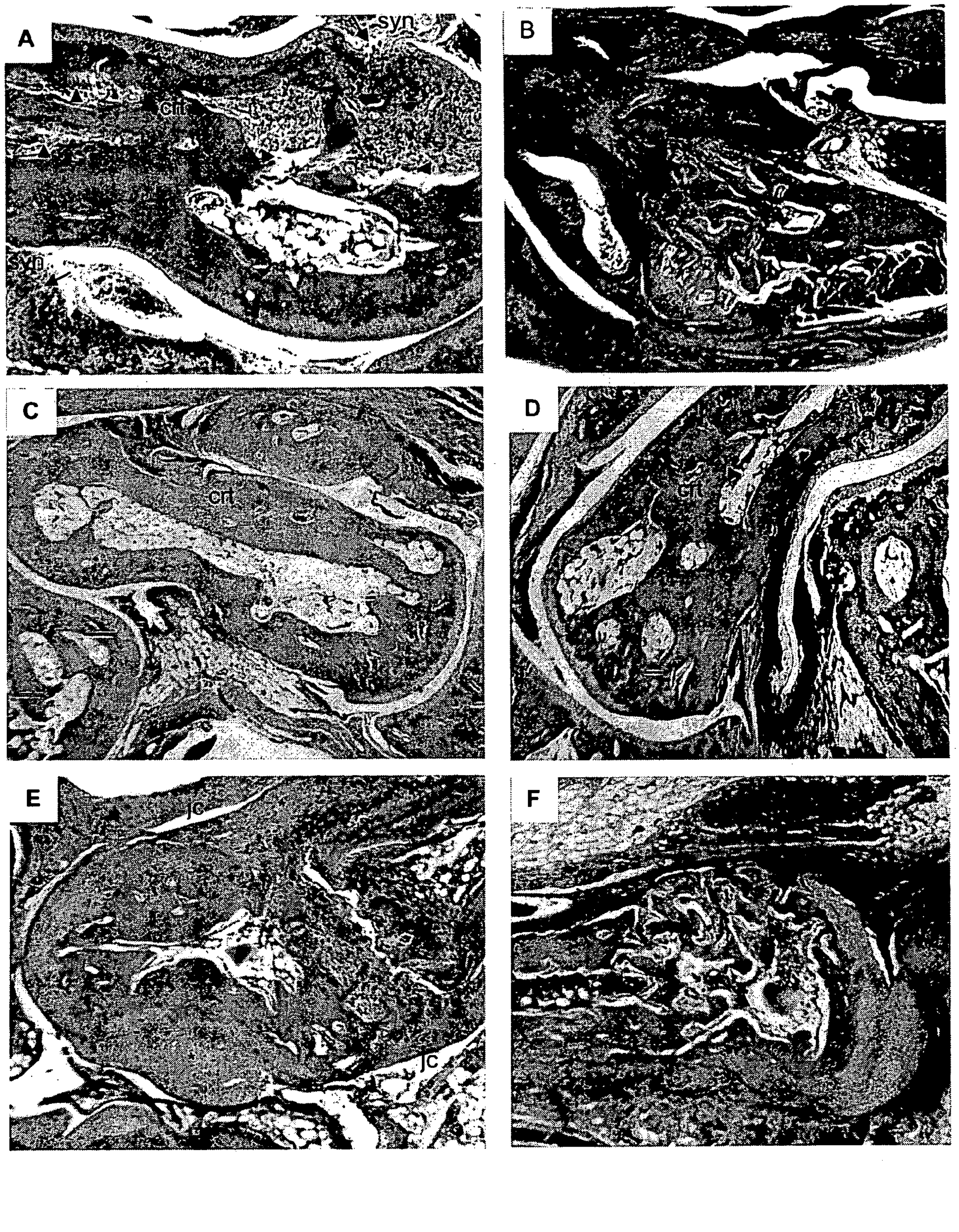
Figure 7:
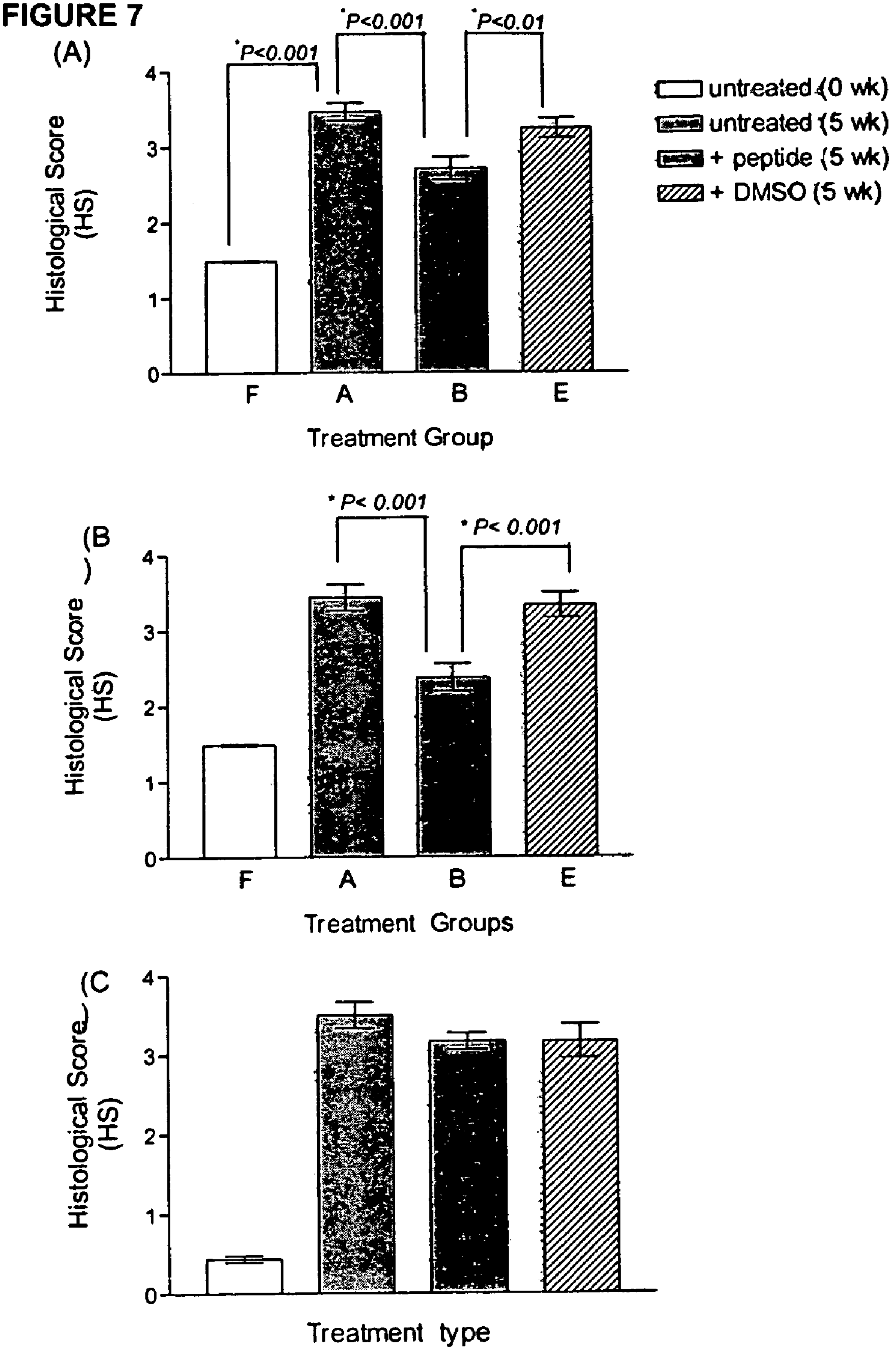

FIG.6 chows histology FIGS. 6A to 6F show histologies of ankle joints. (A) shows untreated Tg197 mice: partially altered articular cartilage with bone erosion and presence of inflammatory infiltrates in the synovial tissue; (B) shows extensive articular cartilage destruction and bone P-NT.II-treated mice: (C) minor cartilage changes with absence of bone erosion; (D) focal articular cartilage destruction and minor bone erosion (arrow head). Scrambled P-NT.II-treated mice: (E) the joint cavity is lined with synovitis, and (F) cartilage destruction and bone erosion are present along with inflammatory infiltrates Non-transgenic controls showed normal joint structures throughout the study.

FIGS. 7A to 7C show the histological scores (HS) of Tg197 mice before and at 5 week-post treatment with the peptide (PNT.II) or vehicle (DMSO). Each group represents mean (±SE) histological scores taken from: (A) 8 (4m+4f) mice (n=16 ankle joints); (B), 4 males (n=8 ankle joints); (C), 4 females (n=8 ankle joints). One-way ANOVA=highly significant ($P<0.0001$). Bonferroni's multiple comparison test shows significant difference ($P<0.05$) between selected groups.

FIG. 8 shows the histologic scores (HS) of Tg197 mice with time course at pre- and 1–4 weeks post-treatment with the peptide P-NT.II. Values are the mean (±SE). N per group is indicated under each bar. One-way ANOVA=highly significant ($P<0.0001$); Bonferroni's multiple comparison test: *($P<0.05$); ($P<0.01$); *($P<0.001$).

FIGS. 9A to 9C show untreated or scrambled peptide-treated Tg197 mice with degenerating synoviocytes showing randomly disintegrated nuclei and vacuolized cytoplasm along with disrupted collagen fibres seen in the synovium, (A); the synovial membrane was lined by closely packed elongated or rounded synoviocytes with infiltrating cells present under the synovium (B); peptide-treated Tg197 group with synoviocyte type-A cells showing characteristic cytoplasmic processes intermingled with those of type-B and neighboring cells (C). Synoviocytes seen at 2–4 weeks post-treatment with the peptide appear unmodified during the course of treatment. The ultrastructural features are similar to those seen in the ankle joints of normal wildtype controls.

FIGS. 10A to 10C show chondrocytes of untreated and treated Tg197 mice. (A) Peptide-treated Tg197 articular chondrocytes showing normal morphology with the nucleus (N), plasma membrane with short cytoplasmic protrusions, rough endoplasmic reticulum, r-ER, and mitochondria, (B) scrambled peptide-treated chondrocytes showing greatly vacuolated cytoplasm and the pycnotic nuclei with cytoplasmic projections coming apart from the cell; (C) degenerated chondrocytes of untreated Tg197 mice showing swollen and disrupted r-ER, and bundles of thickened intermediate filaments. Basement membrane, cytoplasmic organelles and cellular processes were also fragmented. Electron dense areas are seen in the intercellular matrix.

FIG. 11 shows histopathologic score (HS) analysis of different histopathologic parameters. Synovitis, cartilage degradation, and bone erosion were semi-quantitatively assessed in the ankle joints of untreated, P-NT.II- and scrambled P-NT.II-treated Tg197 mice (n=4/group) at 4 weeks post-treatment. HS indicates a protective effect of P-NT.II in all 3 histopathologic parameters of arthritis. Statistical analysis revealed a greater beneficial effect of P-NT.II on cartilage destruction and bone erosion (**$P<0.01$ versus untreated or scrambled P-NT.II-treated groups for both parameters) than on synovitis (*$P<0.05$ versus untreated or scrambled P-NT.II-treated groups).

FIG. 12 depicts time course of serum $sPLA_2$ levels. Serum $sPLA_2$ levels were measured with an *E. coli* membrane assay in blood samples collected from untreated, P-NT.I- and scrambled P-NT.II-treated Tg197 mice at weekly intervals. Values are the mean±SD (n=4/group). One-way ANOVA with Bonferroni's multiple comparison post test: $P<0.05$, untreated versus P-NT.II-treated; $P<0.05$, scrambled P-NT.II-treated versus P-NT.II-treated.

FIGS. 13A and 13B show modulation of LPS- and TNF-stimulated $PGE_2$ release. J774 mouse cell line were incubated with LPS or TNF in absence or presence of varying concentrations (0–40 μM) of P-NT.II, LY315920 or scrambled P-NT.II for 20 h. Supernatants were collected, and $PGE_2$ release in the medium was determined by ELISA. Results are shown as the mean±SEM of 5 experiments performed in duplicate. **$P<0.01$ between inhibitor-treated and untreated cultures.

FIG. 14 shows $PLA_2$ inhibition profiles of the active peptide PIP(59–67) dimer and LY315920 analog against enzymatic activity of purified human synovial $sPLA_2$ (Cayman). Results are the mean±SD of 3 separate experiments done in triplicates. $IC_{50}$ values were graphically determined from the inhibition curves, constructed on the basis of the in vitro results of [$^3$H]-labelled *E. coli* membrane assays.

Thus, the many embodiments of the instant invention stem from the surprising finding that the engineered P-NT.II peptide displays dual mode of inhibitory action against the secretory and cytosolic isoforms of $PLA_2$, which contribute to excitotoxic brain injury, thereby providing protective capacity towards kainite-induced neuronal injury, stroke, and neurodegenerative diseases. Since $sPLA_2$ as well as $cPLA_2$ are known to be involved in the generation of arachidonic acid, the synthesis of $PLA_2$ inhibitor with dual inhibitory activity constitutes a potentially important approach for efficiently treating inflammatory disorders and oxidative stress associated with free radical generation. Using $^3$H-arachidonate-labeled *E. coli* membrane assays and organotypic hippocampal slice cultures, 6–10 μM P-NT.II could offer almost complete protection against kainite lesioned hippocampal slices, indicating protective capacity of the peptide to kainite-induced neural injury.

In animal experiments using transgenic mice, the overall histological evaluation with scores assigned for synovial inflammation, and erosion of bone and cartilage indicated that joints from mice treated with the test peptide for 4–5 weeks had significantly lower histological scores ($P<0.05$) when compared with untreated or mice treated either with a scrambled peptide in DMSO or the vehicle DMSO alone (n=4 males+4 females/group). The results obtained demonstrate modulation of articular cartilage and bone erosion by treatment with the candidate peptide P-NT.II, particularly in the male transgenic Tg197 mice, and suggest a pivotal role for secretory phospholipase $A_2$ inhibitors in the mediation of joint inflammation in rheumatoid arthritis. Results based on gross observations, histological features and morphological evaluations at the cellular level provide compelling evidence that the peptide P-NT.II, its analogs and derivative sequences can potentially be used to treat RA and offer therapeutic and/or prophylactic benefit against inflammation in a chronic autoimmune inflammatory process. These are effective in affording neuroprotection, particularly towards kainate-induced excitotoxic neuronal injury, and in modulating the progression of arthritis.

Novel peptides for utility as an anti-inflammatory and/or neuroprotective agent for potential therapeutic/prophylactic applications in $PLA_2$-mediated pathologies are disclosed. One skilled in the art will readily appreciate that the present invention is well adapted to carry out the objects of the invention and obtain the advantages mentioned, as well as those inherent therein. The compositions, methods etc. described herein are presented as representative of the preferred embodiments, or intended to be exemplary and not intended as limitations on the scope of the present invention.

What is claimed is:

1. An isolated peptide molecule consisting of the amino acid sequence as set forth in SEQ ID NO: 1, wherein said peptide is capable of inhibiting at least one of cytosolic ($cPLA_2$) and secretory phospholipase $A_2$ ($sPLA_2$) activity in a mammal.

2. An isolated peptide fragment or conservatively substituted derivative of the peptide sequence as set forth in SEQ ID NO: 1, wherein said peptide is capable of inhibiting phospholipase $A_2$ ($PLA_2$) activity in a mammal, the conservatively substituted derivative having at least 75% sequence identity to SEQ ID NO: 1.

3. A conservatively substituted peptide derivative of an isolated peptide consisting of the amino acid sequence as set forth in SEQ ID NO: 1, wherein at least one aspartic acid residue is substituted with a glutamic acid residue, the conservatively substituted derivative having at least 75% sequence identity to SEQ ID NO: 1, wherein said peptide is capable of inhibiting phospholipase $A_2$ ($PLA_2$) activity in a mammal.

4. A composition comprising at least one peptide comprising an amino acid sequence of a peptide according to claims 1 and or 2.

5. The composition according to claim 4 further comprising at least one of a pharmaceutically acceptable carrier, diluent and excipient.

6. A composition comprising at least one peptide comprising an amino acid sequence of a peptide according to claim 3.

7. The composition according to claim 6 further comprising at least one pharmaceutically acceptable carrier, diluent and excipient.

8. A method of treatment or prophylaxis of an inflammatory disorder in a mammal by inhibiting the activity of $sPLA_2$, comprising administering to said mammal a therapeutically or prophylactically effective dose, respectively, of the composition according to claim 4.

9. A method of treatment or prophylaxis of an inflammatory disorder in a mammal by inhibiting the activity of $sPLA_2$, comprising administering to said mammal a therapeutically or prophylactically effective dose, respectively, of the composition according to claim 6.

10. The method according to claim 8 wherein the inflammatory disorder is selected from the group consisting of rheumatoid arthritis, acute pancreatitis, chronic inflammatory disease, infection and surgical trauma.

11. The method according to claim 9 wherein the inflammatory disorder is selected from the group consisting of rheumatoid arthritis, acute pancreatitis, chronic inflammatory disease, infection and surgical trauma.

12. A method of treatment or prophylaxis for neuronal injury in a mammal by inhibiting the activity of $sPLA_2$ and/or $cPLA_2$, comprising administering to said mammal, a therapeutically or prophylactically effective dose, respectively, of the composition according to claim 4.

13. A method of treatment or prophylaxis for neuronal injury in a mammal by inhibiting the activity of $sPLA_2$ and/or $cPLA_2$, comprising administering to said mammal, a therapeutically or prophylactically effective doses, respectively, of the composition according to claim 6.

14. The method according to claim 12 wherein the neuronal injury is selected from the group consisting of neurodegenerative disease, trauma, neuronal excitotoxicity and ischemia.

15. The method according to claim 13 wherein the neuronal injury is selected from the group consisting of neurodegenerative disease, trauma, neuronal excitotoxicity and ischemia.

16. A method of treatment or prophylaxis of cancer in a mammal by inhibiting the activity of $sPLA_2$ and/or $cPLA_2$, comprising administering to said mammal, a therapeutically or prophylactically effective dose, respectively, of the composition according to claim 4.

17. A method of treatment or prophylaxis of cancer in a mammal by inhibiting the activity of $sPLA_2$ and/or $cPLA_2$, comprising administering to said mammal, a therapeutically or prophylactically effective dose, respectively, of the composition according to claim 6.

18. The method according to claim 8 wherein the cumulative dose range is between 50 mg and 1 gram.

19. The method according to claim 18 wherein the cumulative dose range is between 120 and 150 mg.

20. The method according to claim 9 wherein the cumulative dose range is between 50 mg and 1 gram.

21. The method according to claim 20 wherein the cumulative dose range is between 120 and 150 mg.

22. The method according to claim 12 wherein the cumulative dose range is between 50 mg and 1 gram.

23. The method according to claim 22 wherein the cumulative dose range is between 120 and 150 mg.

24. The method according to claim 13 wherein the cumulative dose range is between 50 mg and 1 gram.

25. The method according to claim 24 wherein the cumulative dose range is between 120 and 150 mg.

26. The method according to claim 16 wherein the cumulative dose range is between 50 mg and 1 gram.

27. The method according to claim 26 wherein the cumulative dose range is between 120 and 150 mg.

28. The method according to claim 17 wherein the cumulative dose range is between 50 mg and 1 gram.

29. The method according to claim 28 wherein the cumulative dose range is between 120 and 150 mg.

30. The method according to claim 8 wherein the mammal is a human or a rat.

31. The method according to claim 9 wherein the mammal is a human or a rat.

32. The method according to claim 12 wherein the mammal is a human or a rat.

33. The method according to claim 13 wherein the mammal is a human or a rat.

34. The method according to claim 16 wherein the mammal is a human or a rat.

35. The method according to claim 17 wherein the mammal is a human or a rat.

* * * * *

UNITED STATES PATENT AND TRADEMARK OFFICE

CERTIFICATE OF CORRECTION

PATENT NO. : 7,176,281 B2 
APPLICATION NO. : 10/836825
DATED : April 30, 2004
INVENTOR(S) : Ponnampalam Gopalakrishnakone It is certified that error appears in the above-identified patent and that said Letters Patent is hereby corrected as shown below:

Title Page, No. (56), References Cited, Other Publication, Page 2, column 2, reference No. 1 (Information Disclosure Statement dated 04/05/05; page 2, line no. 14);
"Muang-Maung" should be --Maung-Maung--;

Column 2, Line 62;
"NO" should be --NO.--;

Column 3, Line 52;
"T197" should be --Tg197--;

Column 3, Line 54;
"T197" should be --Tg197--;

Column 4, Line 9;
After "$sPLA_2$", insert --.--;

Column 6, Line 43;
"polynudeotide" should be --polynucleotide--;

Column 7, Line 11;
"s PLA " should be --$sPLA_2$--;

Column 7, Line 26;
"sPLAS" should be --$sPLA_2s$--;

Column 7, Line 54;
"s $PLA_2s$" should be --$sPLA_2s$--;

Column 11, Line 54;
Before "FIGS.", insert --(--;

Column 12, Line 53;
After "potency", insert --.--;

Column 13, Line 35;
"$^3$H-LabeLled" should be --$^3$H-labelled--;

Column 18, Line 14
Before "FIGS.", insert --(--;

UNITED STATES PATENT AND TRADEMARK OFFICE

CERTIFICATE OF CORRECTION

PATENT NO. : 7,176,281 B2
APPLICATION NO. : 10/836825
DATED : April 30, 2004
INVENTOR(S) : Ponnampalam Gopalakrishnakone It is certified that error appears in the above-identified patent and that said Letters Patent is hereby corrected as shown below:

Column 18, Line 22;
"Tg 197" should be --Tg197--;

Column 18, Line 34;
"Tg 197" should be --Tg197--;

Signed and Sealed this

Second Day of September, 2008

Jon W. Dudas

JON W. DUDAS
*Director of the United States Patent and Trademark Office*

UNITED STATES PATENT AND TRADEMARK OFFICE

CERTIFICATE OF CORRECTION

PATENT NO. : 7,176,281 B2
APPLICATION NO. : 10/836825
DATED : February 13, 2007
INVENTOR(S) : Ponnampalam Gopalakrishnakone It is certified that error appears in the above-identified patent and that said Letters Patent is hereby corrected as shown below:

Title Page, No. (56), References Cited, Other Publication, Page 2, column 2, reference No. 1 (Information Disclosure Statement dated 04/05/05; page 2, line no. 14);
"Muang-Maung" should be --Maung-Maung--;

Column 2, Line 62;
"NO" should be --NO.--;

Column 3, Line 52;
"T197" should be --Tg197--;

Column 3, Line 54;
"T197" should be --Tg197--;

Column 4, Line 9;
After "$sPLA_2$", insert --.--;

Column 6, Line 43;
"polynudeotide" should be --polynucleotide--;

Column 7, Line 11;
"s PLA" should be --$sPLA_2$--;

Column 7, Line 26;
"sPLAS" should be --$sPLA_2s$--;

Column 7, Line 54;
"s $PLA_2s$" should be --$sPLA_2s$--;

Column 11, Line 54;
Before "FIGS.", insert --(--;

Column 12, Line 53;
After "potency", insert --.--;

Column 13, Line 35;
"$^3H$-LabeLled" should be --$^3H$-labelled--;

Column 18, Line 14;
Before "FIGS.", insert --(--;

UNITED STATES PATENT AND TRADEMARK OFFICE

CERTIFICATE OF CORRECTION

PATENT NO. : 7,176,281 B2
APPLICATION NO. : 10/836825
DATED : February 13, 2007
INVENTOR(S) : Ponnampalam Gopalakrishnakone It is certified that error appears in the above-identified patent and that said Letters Patent is hereby corrected as shown below:

Column 18, Line 22;
"Tg 197" should be --Tg197--;

Column 18, Line 34;
"Tg 197" should be --Tg197--;

This certificate supersedes the Certificate of Correction issued September 2, 2008.

Signed and Sealed this

Thirtieth Day of September, 2008

JON W. DUDAS
*Director of the United States Patent and Trademark Office*

UNITED STATES PATENT AND TRADEMARK OFFICE

CERTIFICATE OF CORRECTION

PATENT NO. : 7,176,281 B2
APPLICATION NO. : 10/836825
DATED : February 13, 2007
INVENTOR(S) : Ponnampalam Gopalakrishnakone It is certified that error appears in the above-identified patent and that said Letters Patent is hereby corrected as shown below:

Title Page, No. (56), References Cited, Other Publication, Page 2, column 2, reference No. 1 (Information Disclosure Statement dated 04/05/05; page 2, line no. 14);
"Muang-Maung" should be --Maung-Maung--;

Column 2, Line 62;
"NO" should be --NO.--;

Column 3, Line 52;
"T197" should be --Tg197--;

Column 3, Line 54;
"T197" should be --Tg197--;

Column 4, Line 9;
After "$sPLA_2$", insert --.--;

Column 6, Line 43;
"polynudeotide" should be --polynucleotide--;

Column 7, Line 11;
"s PLA" should be --$sPLA_2$--;

Column 7, Line 26;
"sPLAS" should be --$sPLA_2s$--;

Column 7, Line 54;
"s $PLA_2s$" should be --$sPLA_2s$--;

Column 11, Line 54;
Before "FIGS.", insert --(--;

Column 12, Line 53;
After "potency", insert --.--;

UNITED STATES PATENT AND TRADEMARK OFFICE
CERTIFICATE OF CORRECTION

PATENT NO. : 7,176,281 B2
APPLICATION NO. : 10/836825
DATED : February 13, 2007
INVENTOR(S) : Ponnampalam Gopalakrishnakone It is certified that error appears in the above-identified patent and that said Letters Patent is hereby corrected as shown below:

Column 13, Line 35;
"$^3$H-LabeLled" should be --$^3$H-labelled--;

Column 18, Line 14;
Before "FIGS.", insert --(--;

Column 18, Line 22;
"Tg 197" should be --Tg197--;

Column 18, Line 34;
"Tg 197" should be --Tg197--;

Column 21, Line 29;
After "scalaradial", insert --[Biomol USA, Cat. No. ST-350]--;

Column 21, Line 30;
Before "at 20", insert --[Agents Actions 39 C39 (1993)]--;

Column 22, Line 21;
Delete "FIG. 6 chows histology";

Column 22, Line 31;
After "infiltrates", insert --.--;

Column 23, Line 22;
"P-NT.I-" should be --P-NT.II- --;

Column 29, Line 43, Claim 4;
"1 and or 2" should be --1 or 2--;

UNITED STATES PATENT AND TRADEMARK OFFICE

CERTIFICATE OF CORRECTION

PATENT NO. : 7,176,281 B2
APPLICATION NO. : 10/836825
DATED : February 13, 2007
INVENTOR(S) : Ponnampalam Gopalakrishnakone It is certified that error appears in the above-identified patent and that said Letters Patent is hereby corrected as shown below:

Column 30, Line 33, Claim 13;
"doses" should be --dose--;

This certificate supersedes the Certificates of Correction issued September 2, 2008 and September 30, 2008.

Signed and Sealed this

Twenty-eighth Day of October, 2008

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 17
<212> TYPE: PRT
<213> ORGANISM: Python reticulatus

<400> SEQUENCE: 1

Leu Gly Arg Val Asp Ile His Val Trp Asp Gly Val Tyr Ile Arg Gly
1               5                   10                  15

Arg


<210> SEQ ID NO 2
<211> LENGTH: 13
```

-continued

```
<212> TYPE: PRT
<213> ORGANISM: Python reticulatus

<400> SEQUENCE: 2

Gly Asp Asp Cys Asp Gly Tyr Gln Glu Glu Cys Pro Ser
1               5                   10


<210> SEQ ID NO 3
<211> LENGTH: 16
<212> TYPE: PRT
<213> ORGANISM: Python reticulatus

<400> SEQUENCE: 3

Ser Pro Glu Asp Arg Cys Gly Lys Ile Leu Ile Asp Ile Ala Leu Ala
1               5                   10                  15


<210> SEQ ID NO 4
<211> LENGTH: 13
<212> TYPE: PRT
<213> ORGANISM: Python reticulatus

<400> SEQUENCE: 4

Leu Pro Gly Leu Pro Leu Ser Leu Gln Asn Gly Leu Tyr
1               5                   10


<210> SEQ ID NO 5
<211> LENGTH: 15
<212> TYPE: PRT
<213> ORGANISM: Python reticulatus

<400> SEQUENCE: 5

Gly Ala Phe Gly Ile Phe Thr Glu Asp Ser Thr Glu His Glu Val
1               5                   10                  15


<210> SEQ ID NO 6
<211> LENGTH: 13
<212> TYPE: PRT
<213> ORGANISM: Python reticulatus

<400> SEQUENCE: 6

Gly Asn Ile Thr Tyr Asn Ile Lys Gly Cys Val Ser Ser
1               5                   10


<210> SEQ ID NO 7
<211> LENGTH: 15
<212> TYPE: PRT
<213> ORGANISM: Python reticulatus

<400> SEQUENCE: 7

Pro Leu Val Thr Leu Ser Glu Arg Gly His Glu Gly Arg Lys Asn
1               5                   10                  15


<210> SEQ ID NO 8
<211> LENGTH: 9
<212> TYPE: PRT
<213> ORGANISM: Python reticulatus

<400> SEQUENCE: 8

Val Asp Ile His Val Trp Asp Gly Val
1               5


<210> SEQ ID NO 9
<211> LENGTH: 18
<212> TYPE: PRT
<213> ORGANISM: Python reticulatus
```

-continued

<400> SEQUENCE: 9

```
Val Asp Ile His Val Trp Asp Gly Val Val Asp Ile His Val Trp Asp
1               5                   10                  15

Gly Val
```

<210> SEQ ID NO 10
<211> LENGTH: 51
<212> TYPE: DNA
<213> ORGANISM: Python reticulatus

<400> SEQUENCE: 10

```
cctggccgtg ttgacataca tgtttgggat ggagtgtata taagaggaag a              51
```

<210> SEQ ID NO 11
<211> LENGTH: 39
<212> TYPE: DNA
<213> ORGANISM: Python reticulatus

<400> SEQUENCE: 11

```
ggagatgact gtgatggtta tcaggaggaa tgtccctct                            39
```

<210> SEQ ID NO 12
<211> LENGTH: 48
<212> TYPE: DNA
<213> ORGANISM: Python reticulatus

<400> SEQUENCE: 12

```
tctccagaag accgatgtgg caagattctg atagacatcg cattagca                  48
```

<210> SEQ ID NO 13
<211> LENGTH: 39
<212> TYPE: DNA
<213> ORGANISM: Python reticulatus

<400> SEQUENCE: 13

```
cttcctggat tgcccctctc cctccagaat gggctctat                            39
```

<210> SEQ ID NO 14
<211> LENGTH: 45
<212> TYPE: DNA
<213> ORGANISM: Python reticulatus

<400> SEQUENCE: 14

```
ggtgcttttg gtatttttac cgaggacagc actgaacatg aagtt                     45
```

<210> SEQ ID NO 15
<211> LENGTH: 39
<212> TYPE: DNA
<213> ORGANISM: Python reticulatus

<400> SEQUENCE: 15

```
ggaaacatca cttataatat caaaggctgt gtttcttcc                            39
```

<210> SEQ ID NO 16
<211> LENGTH: 45
<212> TYPE: DNA
<213> ORGANISM: Python reticulatus

<400> SEQUENCE: 16

```
cccttggtaa ctttgagtga aagaggtcat gaaggacgca aaaat                     45
```

-continued

```
<210> SEQ ID NO 17
<211> LENGTH: 27
<212> TYPE: DNA
<213> ORGANISM: Python reticulatus

<400> SEQUENCE: 17

gttgacatac atgtttggga tggagtg                                          27


<210> SEQ ID NO 18
<211> LENGTH: 27
<212> TYPE: DNA
<213> ORGANISM: Python reticulatus

<400> SEQUENCE: 18

gttgacatac atgtttggga tggagtg                                          27
```